US008778954B2

(12) United States Patent
Miura et al.

(10) Patent No.: US 8,778,954 B2
(45) Date of Patent: Jul. 15, 2014

(54) PHENYLPYRIDINE DERIVATIVE AND MEDICINAL AGENT COMPRISING SAME

(75) Inventors: Toru Miura, Higashimurayama (JP); Seiichi Sato, Higashimurayama (JP); Hajime Yamada, Higashimurayama (JP); Junya Tagashira, Higashimurayama (JP); Ryohei Sekimoto, Higashimurayama (JP); Rie Ishida, Higashimurayama (JP); Hitomi Aoki, Higashimurayama (JP); Tadaaki Ohgiya, Higashimurayama (JP)

(73) Assignee: Kowa Company, Ltd., Nagoya-shi (JP)

( * ) Notice: Subject to any disclaimer, the term of this patent is extended or adjusted under 35 U.S.C. 154(b) by 194 days.

(21) Appl. No.: 13/394,266

(22) PCT Filed: Sep. 29, 2010

(86) PCT No.: PCT/JP2010/005842
§ 371 (c)(1),
(2), (4) Date: Mar. 5, 2012

(87) PCT Pub. No.: WO2011/040004
PCT Pub. Date: Apr. 7, 2011

(65) Prior Publication Data
US 2012/0165353 A1 Jun. 28, 2012

(30) Foreign Application Priority Data

Sep. 29, 2009 (JP) ................. 2009-223887

(51) Int. Cl.
*C07D 401/14* (2006.01)
*A61K 31/422* (2006.01)
*A61K 31/4427* (2006.01)
(52) U.S. Cl.
CPC ............ *C07D 401/14* (2013.01); *A61K 31/422* (2013.01); *A61K 31/4427* (2013.01)
USPC ............................ 514/269; 544/296; 544/319
(58) Field of Classification Search
CPC . C07D 401/14; A61K 31/422; A61K 31/4427
USPC .................... 544/296, 319; 514/269
See application file for complete search history.

(56) References Cited

U.S. PATENT DOCUMENTS

| 5,212,177 A | 5/1993 | Poss et al. |
| 5,736,555 A | 4/1998 | Naka et al. |
| 2008/0207654 A1 | 8/2008 | Kuroita et al. |
| 2009/0176760 A1 | 7/2009 | Yanagisawa et al. |
| 2010/0137281 A1 | 6/2010 | Kuroita et al. |

FOREIGN PATENT DOCUMENTS

| EP | 0 465 323 A1 | 1/1992 |
| JP | 5-271228 A | 10/1993 |
| JP | 5-331165 A | 12/1993 |
| JP | 6-211845 A | 8/1994 |
| JP | 7-179456 A | 7/1995 |
| WO | 2008/062905 A2 | 5/2008 |
| WO | 2008/084303 A1 | 7/2008 |
| WO | 2008/096820 A1 | 8/2008 |
| WO | 2008/096829 A1 | 8/2008 |
| WO | 2008/143262 A1 | 11/2008 |

OTHER PUBLICATIONS

Fayer et al., PubMed Abstract (J Clin Pharmacol. 41(3):305-16), 2001.*
Notification of Transmittal of Translation of the International Preliminary Report on Patentability (Forms PCT/IB/338) of International Application No. PCT/JP2010/005842 mailed Apr. 12, 2012 with Forms PCT/IB/326, PCT/IB/373 and PCT/ISA/237.
Extended European Search Report dated Feb. 6, 2013, issued in corresponding European Patent Application No. 10820125.2 (5 pages).
Schmieder Roland E., "Mechanisms for the Clinical Benefits of Angiotensin II Receptor Blockers" AJH 2005; 720-730.
Siragy Helmy M., MD "Evidence for Benefits of Angiotensin Receptor Blockade Beyond Blood Pressure Control"Current Hypertension Reports 2008, 10:261-267.
The Shiga Microalbuminuria Reduction Trial (SMART) Group "Reduction of Microalbuminuria in Patients With Type 2 Diabetes" Diabetes Care, No. 6, Jun. 2007, vol. 30, p. 1581.
PA Sarafidis et al., "Protection of the kidney by thiazolidinediones: An assessment from bench to bedside" International Society of Nephrology 2006, 70, 1223-1233.
Nesto Richard W. et al., "Thiazolidinedione Use, Fluid Retention, and Congestive Heart Failure: A Consensus Statement From the American Heart Association and American Diabetes Association" Circulation, Journal of the American Heart Association, 2003;108;2941-2948.
Gross Barbara et al., "PPAR agonists: multimodal drugs for the treatment of type-2 diabetes" Best Practice & Research Clinical Endocrinology & Metabolism, 2007, vol. 21, No. 4, p. 687-710.

(Continued)

Primary Examiner — Deepak Rao
(74) Attorney, Agent, or Firm — Westerman, Hattori, Daniels & Adrian, LLP

(57) ABSTRACT

Disclosed are: a novel compound which has both an antagonistic activity on an angiotensin II receptor and a PPARγ-activating activity and is therefore useful as a prophylactic and/or therapeutic agent for hypertension, heart diseases, arteriosclerosis, type-2 diabetes, diabetic complications, metabolic syndrome or the like; and a pharmaceutical composition containing the compound. Specifically disclosed are: a compound represented by general formula (I) (wherein the ring A represents a pyridine ring; the ring B represents a tetrazole ring or an oxadiazol-5(4H)-one ring; X represents C—$R^5$ or a nitrogen atom; $R^1$ represents a $C_{1-6}$ alkyl group; $R^2$ represents a $C_{1-6}$ alkyl group or a $C_{3-8}$ cycloalkyl group; and $R^3$, $R^4$, $R^5$ independently represent a hydrogen atom, a halogen atom, a $C_{1-6}$ alkyl group, a halo-$C_{1-6}$ alkyl group, or a $C_{1-6}$ alkoxy group which may have a substituent), a salt of the compound, or a solvate of the compound or the salt; and a pharmaceutical composition containing the compound, the salt or the solvate.

3 Claims, 4 Drawing Sheets

(56) References Cited

OTHER PUBLICATIONS

Walcher Daniel et al., "Insulin resistance and cardiovascular disease: the role of PPARγ activators beyond their anti-diabetic action" Diabetes and Vascular Disease Research, 2004;2: 76-81.

Patel Chetan et al., "Thiazolidinediones, peripheral oedema and congestive heart failure: what is the evidence?" vol. 2, Issue 2, May 2005, p. 61.

Semple Robert K. et al., "PPARy and human metabolic disease" The Journal of Clinical Investigation, vol. 116 No. 3, Mar. 2006, p. 581.

Sotiropoulos Konstantinos B. et al., "Adipose-specific effect of rosiglitazone on vascular premeability and protein kinase C activation: novel mechanism for PPARy agonist's effects on edema and weight gain" The FASEB Journal, 0892-6638, 20, 2006, p. 1203.

Benson Stephen C. et al., "Identification of Telmisartan as a Unique Angiotensin II Receptor Antagonist With Selective PPARy-Modulating Activity" Hypertension 43, 2004, p. 993.

Schupp Michael et al., "Angiotensin Type 1 Receptor Blockers Induce Peroxisome Proliferator—Activated Receptor-y Activity" Circulation 109, 2004, p. 2054.

International Search Report of PCT/JP2010/005842, mailing date Nov. 2, 2010.

\* cited by examiner

Data are expressed as mean ±S.E.M.

PHENYLPYRIDINE DERIVATIVE AND MEDICINAL AGENT COMPRISING SAME

TECHNICAL FIELD

The present invention relates to a novel phenylpyridine derivative that has both angiotensin II receptor antagonistic activity and PPARγ activation activity, and a pharmaceutical agent containing the same.

BACKGROUND ART

In recent years, disorders like diabetes, hypertension, dyslipidemia and obesity which can be a risk factor for arteriosclerotic disorders have been rapidly increasing due to changes in life style with improvements in living standard, i.e., high calorie and high cholesterol type diet, obesity, lack of exercise, aging, and the like. It is known that, although being a risk factor independent of each other, overlap of the disorders can cause an occurrence of arteriosclerotic disorders at higher frequency or aggravation of the disorders. As such, with the understanding of a condition having a plurality of risk factors for arteriosclerotic disorders as metabolic syndrome, efforts have been made to elucidate the cause of the syndrome and to develop a therapeutic method therefor.

Angiotensin II (herein below, it may be also abbreviated as AII) is a peptide that is found to be an intrinsic pressor substance produced by renin-angiotensin system (i.e., RA system). It is believed that pharmacological inhibition of angiotensin II activity can lead to treatment or prevention of circulatory disorders like hypertension. Accordingly, an inhibitor for angiotensin converting enzyme (ACE) which inhibits the enzyme promoting the conversion of angiotensin I (AI) to angiotensin II has been clinically used as an inhibitory agent for RA system. Furthermore, an orally administrable AII receptor blocker (Angiotensin Receptor Blocker: ARB) has been developed, and losartan, candesartan, telmisartan, valsartan, olmesartan, and irbesartan, and the like are already clinically used as a hypotensive agent. It is reported by many clinical or basic studies that, as having not only a hypotensive activity but also other various activities including an anti-inflammatory activity, an endothelial function improving activity, a cardiovascular remodeling inhibiting activity, an oxidation stress inhibiting activity, a proliferation factor inhibiting activity, and insulin resistance improving activity, and the like, ARB is useful for cardiovascular disorders, renal diseases, and arteriosclerosis, and the like (Non-Patent Documents 1 and 2). Most recently, it is also reported that ARB particularly has a kidney protecting activity which does not depend on a hypotensive activity (Non-Patent Document 3).

Meanwhile, three isoforms, i.e., α, γ, and γ, have been identified so far as peroxisome proliferator-activated receptors (PPARγ) which belong to a nuclear receptor superfamily. Among them, PPARγ is an isoform that is most abundantly expressed in an adipose tissue and it plays an important role in differentiation of adipocytes or metabolism of glycolipids. Currently, thiazolidinedione derivatives (i.e., TZD) like pioglitazone or rosiglitazone are clinically used as a therapeutic agent for diabetes having PPARγ activation activity, and they are known to have an activity of improving insulin resistance, glucose tolerance, and lipid metabolism, and the like. Further, it is recently reported that, based on activation of PPARγ, TZD exhibits various activities including a hypotensive activity, an anti-inflammatory activity, an endothelial function improving activity, a proliferation factor inhibiting activity, and an activity of interfering RA system, and the like.

It is also reported that, according to such multiple activities, TZD shows a kidney protecting activity particularly in diabetic nephropathy without depending on blood sugar control (Non-Patent Documents 4, 5, 6, 7, and 8). Meanwhile, there is also a concern regarding adverse effects of TZD caused by PPARγ activation like body fluid accumulation, body weight gain, peripheral edema, and pulmonary edema (Non-Patent Documents 9 and 10).

It has been recently reported that telmisartan has a PPARγ activation activity (Non-Patent Document 11). It has been also reported that the irbesartan has the same activity (Non-Patent Document 12). These compounds have both a RA system inhibiting activity and a PPARγ activation activity, and thus are expected to be used as an integrated agent for prevention and/or treatment of circulatory disorders (e.g., hypertension, heart diseases, angina pectoris, cerebrovascular disorders, cerebral circulatory disorders, ischemic peripheral circulatory disorders, and renal diseases, and the like) or diabetes-related disorders (e.g., Type II diabetes, diabetic complications, insulin resistant syndrome, metabolic syndrome, hyperinsulinemia, and the like) without increasing a risk of body fluid accumulation, body weight gain, peripheral edema, pulmonary edema, or congestive heart failure that are concerned over the use of TZD (Patent Document 1). Among them, for diabetic nephropathy, a synergistic prophylactic and/or therapeutic effect is expected from multiple kidney protecting activity based on activities of RA system inhibition and PPARγ activation.

As compounds having such activities, pyrimidine and triazine derivatives (Patent Document 1), imidazopyridine derivatives (Patent Document 2), indole derivatives (Patent Document 3), imidazole derivatives (Patent Document 4), and condensed ring derivatives (Patent Document 5) have been reported. However, the phenylpyridine derivative of the present invention is neither described nor suggested.

Meanwhile, Patent Document 6 discloses compounds represented by the following formula (A):

(A)

[Chemical Formula 1]

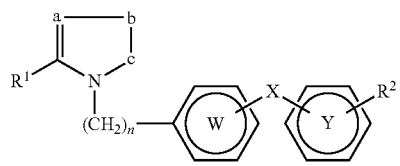

[wherein, $R^1$ represents a hydrocarbon residue that may be bonded through a heteroatom or substituted, $R^2$ represents a 5 to 7-membered heterocyclic residue that may be substituted having as a ring constituting group, a carbonyl group, a thiocarbonyl group, a sulfur atom that can be oxidized, or a ring constituting group that can be converted thereto, X represents bonding of ring Y and ring W directly or through a spacer of 2 or less atom chains, W and Y represent an aromatic hydrocarbon residue or a heterocyclic residue that may be substituted or may contain a heteroatom, n represents an integer of 1 or 2, a and b, which constitute the heterocyclic residue, represent, independently from each other, one or two carbons or heteroatoms that may be substituted, c represents one carbon or heteroatom that may be substituted, and substituents on two adjacent ring constituting atoms in the group represented by the formula:

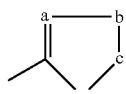

may bond to each other to form a 5 to 6-membered ring with the two ring constituting atoms]. Biphenyl is raised as a preferably example of the W—Y ring system, and the Examples specifically describe only a biphenyl derivative. These compounds disclosed in Patent Document 6 are different from the compound of the present invention in view of the ring to which the pyridinylmethyl group is bonded. Furthermore, in Patent Document 6, PPARγ activation activity as a pharmacological activity, or a treatment for diabetes, obesity or metabolic syndrome is neither described nor suggested.

PRIOR ART LITERATURE

Patent Literature

Patent Document 1: WO 2008/062905
Patent Document 2: WO 2008/084303
Patent Document 3: WO 2008/096820
Patent Document 4: WO 2008/096829
Patent Document 5: WO 2008/143262
Patent Document 6: Japanese Patent Application Laid-Open (JP-A) No. 5-271228

Non-Patent Document

Non-Patent Document 1: AMER. J. Hypertension, 18, 720 (2005)
Non-Patent Document 2: Current Hypertension Report, 10, 261(2008)
Non-Patent Document 3: Diabetes Care, 30, 1581(2007)
Non-Patent Document 4: Kidney Int., 70, 1223 (2006)
Non-Patent Document 5: Circulation, 108, 2941(2003)
Non-Patent Document 6: Best Pract. Res. Clin. Endocrinol. Metab., 21(4), 687 (2007)
Non-Patent Document 7: Diab. Vasc. Dis. Res., 1(2), 76 (2004)
Non-Patent Document 8: Diab. Vasc. Dis. Res., 2 (2), 61 (2005)
Non-Patent Document 9: J. Clin. Invest., 116 (3), 581 (2006)
Non-Patent Document 10: FASEB J., 20 (8), 1203 (2006)
Non-Patent Document 11: Hypertension, 43, 993 (2004)
Non-Patent Document 12: Circulation, 109, 2054 (2004)

SUMMARY OF THE INVENTION

Problems to be Solved by the Invention

An object of the present invention is to provide a novel compound that is useful as a pharmaceutical agent for preventing and/or treating hypertension as a circulatory disorder, diabetes as a metabolic disease, or the like, and a pharmaceutical composition using the same.

Means for Solving the Problems

As a result of intensive studies to achieve the purpose described above, the inventors of the invention found that the compound represented by the formula (I) below is a compound that has excellent angiotensin II receptor antagonistic activity and PPARγ activation activity, and therefore completed the invention.

Specifically, the present invention relates to the following inventions.

[1] A compound represented by the formula (I) below or a salt thereof, or a solvate thereof:

(I)

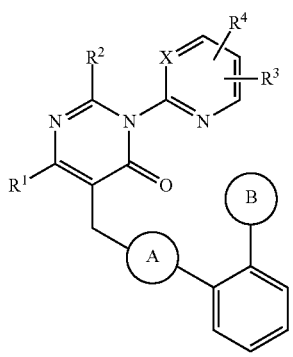

[in the formula, ring A represents the following formula (II) or the following formula (III):

(II)

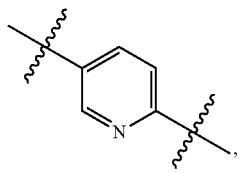

(III)

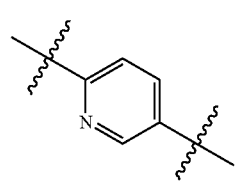

ring B represents the following formula (IV) or the following formula (V):

(IV)

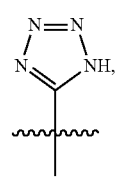

(V)

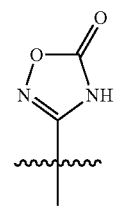

X represents C—$R^5$ or a nitrogen atom,
$R^1$ represents a $C_{1-6}$ alkyl group, R² represents a C₁₋₆ alkyl group or a C₃₋₈ cycloalkyl group,
R³, R⁴, and R⁵ represent, independently from each other, a hydrogen atom, a halogen atom, a C₁₋₆ alkyl group, a halo C₁₋₆ alkyl group, or a C₁₋₆ alkoxy group which may have a substituent group, respectively. Further, the wavy lines in the formulae represent bonding positions with an adjacent group].

[2] The compound according to [1] or the salt thereof, or the solvate thereof, wherein the compound represented by the formula (I) is a compound that is selected from a group consisting of:

5-{{6-[2-(1H-tetrazol-5-yl)phenyl]pyridin-3-yl}methyl}-6-butyl-3-(5-methoxypyrimidin-2-yl)-2-methylpyrimidin-4(3H)-one, 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one, 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one, 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one, 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one, 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one, 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one, 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one, 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one, 5-{{5-[2-(1H-tetrazol-5-yl)phenyl]pyridin-2-yl}methyl}-6-butyl-2-methyl-3-(pyridin-2-yl)pyrimidin-4(3H)-one, 5-{{5-[2-(1H-tetrazol-5-yl)phenyl]pyridin-2-yl}methyl}-6-butyl-3-(5-methoxypyridin-2-yl)-2-methylpyrimidin-4(3H)-one, 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one, 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one, 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one, 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one, 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5(4H)-one, and 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one.

The alkyl group such as butyl in the nomenclature of the above-mentioned compounds represents a straight (normal) chain unless particularly designated.

[3] A pharmaceutical composition containing the compound or the salt thereof, or the solvate thereof described in the above [1] or [2], and a pharmaceutically acceptable carrier.

[4] A pharmaceutical composition containing: the compound or the salt thereof, or the solvate thereof described in the above [1] or [2] as an effective component, having both angiotensin II receptor antagonistic activity and PPARγ activation activity.

[5] An agent for preventing and/or treating a circulatory disorder containing as an effective component the compound or the salt thereof, or the solvate thereof described in the above [1] or [2].

[6] The agent for preventing and/or treating a circulatory disease described in the above [5], wherein the circulatory disease is hypertension, heart disease, angina pectoris, cerebral vascular accident, cerebrovascular disorder, ischemic peripheral circulatory disorder, kidney disease, or arteriosclerosis.

[7] An agent for preventing and/or treating a metabolic disease containing as an effective component the compound or the salt thereof, or the solvate thereof described in the above [1] or [2].

[8] The agent for preventing and/or treating a metabolic disease described in the above [7], wherein the metabolic disease is Type II diabetes mellitus, diabetic complication (diabetic retinopathy, diabetic neuropathy, or diabetic nephropathy), insulin resistant syndrome, metabolic syndrome, or hyperinsulinemia.

[9] A method of preventing and/or treating a circulatory disease characterized in that an effective amount of the compound or the salt thereof, or the solvate thereof described in the above [1] or [2] is administered to a patient in need of the treatment.

[10] A method of preventing and/or treating a metabolic disease characterized in that an effective amount of the compound or the salt thereof, or the solvate thereof described in the above [1] or [2] is administered to a patient in need of the treatment.

[11] Use of the compound or the salt thereof, or the solvate thereof described in the above [1] or [2] for production of a preparation used for prevention and/or treatment of a circulatory disease.

[12] Use of the compound or the salt thereof, or the solvate thereof described in the above [1] or [2] for production of a preparation used for prevention and/or treatment of a metabolic disease.

[13] The compound or the salt thereof, or the solvate thereof described in the above [1] or [2] as a preventive and/or therapeutic agent having both an angiotensin II receptor antagonist activity and a PPARγ activation activity.

Effects of the Invention

The phenylpyridine derivative represented by the formula (I) of the invention or a salt thereof, or a solvate thereof exhibits a potent antagonistic activity for an angiotensin II receptor, and can be appropriately used as an effective component for an agent for preventing and/or treating a disease related with angiotensin II, for example a circulatory disease such as hypertension, heart disease, angina pectoris, cerebral vascular accident, cerebrovascular disorder, ischemic peripheral circulatory disorder, kidney disease, and arteriosclerosis.

Further, the phenylpyridine derivative represented by the formula (I) of the invention or a salt thereof, or a solvate thereof has a PPARγ activation activity and can be appropriately used as an effective component for an agent for preventing and/or treating a disease related with PPARγ, for example metabolic disease such as arteriosclerosis, Type II diabetes mellitus, diabetic complication (diabetic retinopathy, diabetic neuropathy, or diabetic nephropathy), insulin resistance syndrome, syndrome X, metabolic syndrome, and hyperinsulinemia.

Still further, the phenylpyridine derivative represented by the formula (I) of the invention, or a salt thereof, or a solvate thereof has both an antagonistic activity for an angiotensin II receptor and PPARγ activation activity and can be appropriately used as an effective component for an agent for preventing and/or treating a disease related with both angiotensin II and PPARγ, for example, arteriosclerosis, diabetic nephropathy, insulin resistance syndrome, syndrome X, and metabolic syndrome.

BRIEF DESCRIPTION OF THE DRAWINGS

FIG. 4-1 illustrates results of investigations for activity for diabetic nephropathy. The horizontal axis of FIG. 4-1 represents time (weeks after administration), and the vertical axis represents the elimination amount of urinary total protein per 18 hours. The data in FIG. 4-1 represents average values of each individual in each point, wherein -●- represents Vehicle (solvent control), -♦- represents Telmisartan, -■- represents Compound 23 (the compound of Example 23), and -▲- represents Compound 21 (the compound of Example 21).

FIG. 4-2 illustrates results of investigations of activity for diabetic nephropathy. The vertical axis of FIG. 4-2 represents the elimination amount of urinary total protein per 18 hours, and Vehicle, Telmisartan, Compound 23, and Compound 21 of the horizontal axis represent solvent control, telmisartan, the compound of Example 23, and the compound of Example 21, respectively. The data in FIG. 4-2 represents individual values and average values of each individual +standard deviation.

MODES FOR CARRYING OUT THE INVENTION

Figure 1:
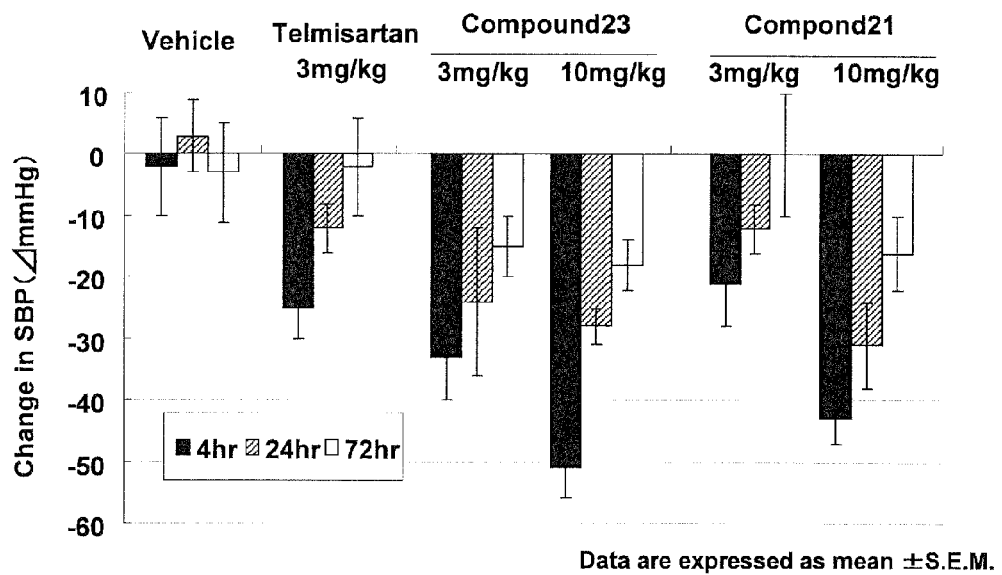
FIG. 1 illustrates results of investigations of hypotensive activity with tail cuff method. The vertical axis of FIG. 1 represents the change of the values from pre-administration in systolic blood pressure, and Vehicle, Telmisartan, Compound 23, and Compound 21 of the horizontal axis represent solvent control, telmisartan, the compound of Example 23, and the compound of Example 21, respectively. The data in FIG. 1 represents average values of each individual ±standard error, and the black color represents results after 4 hours, the ash color represents results after 24 hours, and the white color represents results after 72 hours.

The "halogen atom" as used herein includes a fluorine atom, a chlorine atom, a bromine atom, an iodine atom, and the like.

The "$C_{1-6}$ alkyl group" and the "$C_{1-6}$ alkyl" as used herein mean a linear or branched hydrocarbon group having 1 to 6 carbon atoms, and examples thereof include a methyl group, an ethyl group, a n-propyl group, an isopropyl group, a n-butyl group, an isobutyl group, a t-butyl group, a n-pentyl group, a 2-methylbutyl group, a 2,2-dimethylpropyl group, a n-hexyl group, and the like.

The "$C_{3-8}$ cycloalkyl group" and the "$C_{3-8}$ cycloalkyl" as used herein include saturated or unsaturated monocyclic, polycyclic, or condensed cyclic cycloalkyl group having 3 to 8 carbon atoms, and preferably 3 to 6 carbon atoms. Examples of such cycloalkyl group include a cyclopropyl group, a cyclobutyl group, a cyclopentyl group, a cyclohexyl group, a cycloheptyl group, and a cyclooctyl group.

The "halo $C_{1-6}$ alkyl group" and the "halo $C_{1-6}$ alkyl" as used herein mean a linear or a branched alkyl group having 1 to 6 carbon atoms substituted with one to the largest possible number of halogen atoms, and examples thereof include a fluoromethyl group, a difluoromethyl group, a trifluoromethyl group, a 2,2,2-trifluoroethyl group, a 1,1,2,2,2-pentafluoroethyl group, a 3,3,3-trifluoropropyl group, and the like.

The "$C_{1-6}$ alkoxy group" as used herein means a linear or branched alkoxy group having 1 to 6 carbon atoms, and examples thereof include a methoxy group, an ethoxy group, a propoxy group, an isopropoxy group, a butoxy group, an isobutoxy group, a sec-butoxy group, a tert-butoxy group, a pentoxy group, an isopentoxy group, a neopentoxy group, a hexyloxy group, an isohexyloxy group, and the like.

The "substituent group" for the "$C_{1-6}$ alkoxy group which may have substituent group" as used herein may be the same or different from each other, and the alkoxy group may be substituted with one to largest possible number of substituent groups. Examples of the "substituent group" include a phenyl group; a hydroxyl group; a $C_{2-6}$ alkoxy group; a $C_{2-6}$ alkylthio group; a $C_{1-6}$ alkylsulfonyl group; an oxazolyl group (which may be substituted with a 5 to 10-membered heteroaryl group that may be substituted with a $C_{2-6}$ alkyl group; a $C_{6-20}$ aryl group; or a halogen atom); a pyridyl group (which may be substituted with a $C_{2-6}$ alkyl group); a $C_{2-6}$ alkoxycarbonyl group; a carboxyl group; a carbamoyl group; a mono $C_{2-6}$ alkylcarbamoyl group; a di $C_{2-6}$ alkylcarbamoyl group; a $C_{2-6}$ alkanoylamino group; a $C_{1-6}$ alkylsulfonylamino group; a halo $C_{2-6}$ alkylsulfonylamino group; an amide group; a sulfonamide group; and the like.

Examples of the preferred mode of the invention include the followings.

As for the $R^1$ of the formula (I), preferred examples of the $C_{2-6}$ alkyl group include a $C_{2-4}$ alkyl group, and more preferred examples include a $C_{2-4}$ alkyl group. For example, an ethyl group, a n-propyl group and a n-butyl group are preferable, and a n-butyl group is particularly preferable.

As for $R^2$ in the formula (I), preferred examples of the $C_{1-6}$ alkyl group include $C_{1-4}$ alkyl group. For example, a methyl group, an ethyl group, and an isopropyl group are preferable.

As for $R^2$ in the formula (I), preferred examples of the $C_{3-8}$ cycloalkyl group include $C_{3-6}$ cycloalkyl. For example, a cyclopropyl group, a cyclobutyl group, a cyclopentyl group, and a cyclohexyl group are preferable.

As for $R^3$ and $R^4$ in the formula (I), preferred examples of the $C_{1-6}$ alkyl group include a $C_{1-4}$ alkyl group. For example, a methyl group and an ethyl group are preferable.

As for $R^3$ and $R^4$ in the formula (I), preferred examples of the halo $C_{1-6}$ alkyl group include a halo $C_{1-4}$ alkyl group. For example, a difluoromethyl group, a trifluoromethyl group, and a 2,2,2-trifluoroethyl group are preferable, and a trifluoromethyl group is particularly preferable.

As for $R^3$ and $R^4$ in the formula (I), preferred examples of the "$C_{1-6}$ alkoxy group" in the $C_{1-6}$ alkoxy group which may have a substituent group include a $C_{1-4}$ alkoxy group. For example, a methoxy group, an ethoxy group, a propoxy group, an isopropoxy group, and a n-butoxy group are preferable. As for the "substituent group", preferred examples include a phenyl group, a hydroxyl group, a $C_{1-6}$ alkylthio group (for example, a methylthio group), and a $C_{1-6}$ alkylsulfonyl group (for example, a methylsulfonyl group).

More preferred examples of the compounds that are represented by the formula (I) include a compound that is selected from a group consisting of following compounds:

5-{{6-[2-(1H-tetrazol-5-yl)phenyl]pyridin-3-yl}methyl}-6-butyl-3-(5-methoxypyrimidin-2-yl)-2-methylpyrimidin-4(3H)-one, 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one, 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one, 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one, 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one, 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one, 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one, 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one, 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one, 5-{{5-[2-(1H-tetrazol-5-yl)phenyl]pyridin-2-yl}methyl}-6-butyl-2-methyl-3-(pyridin-2-yl)pyrimidin-4(3H)-one, 5-{{5-[2-(1H-tetrazol-5-yl)phenyl]pyridin-2-yl}methyl}-6-butyl-3-(5-methoxypyridin-2-yl)-2-methylpyrimidin-4(3H)-one, 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one, 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one, 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one, 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one, 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5(4H)-one, and 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one.

More preferred examples of the 5-(pyridinylmethyl)pyrimidin-4(3H)-one derivative that are represented by the formula (I) include a compound that is selected from a group consisting of following compounds:

3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, and 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one.

If the compound of the invention has geometrical isomers or optical isomers, the invention encompasses all of such isomers. Isolation of these isomers is carried out by an ordinary method.

Salts of the compound represented by the formula (I) are not particularly limited, if they are pharmaceutically acceptable salts. When the compound is processed as an acidic compound, an alkali metal salt or an alkali earth metal salt like sodium salt, potassium salt, magnesium salt, and calcium salt; and a salt with an organic base like trimethylamine, triethylamine, pyridine, picoline, N-methylpyrrolidine, N-methylpiperidine, and N-methylmorpholine can be mentioned. When the compound is processed as a basic compound, an acid addition salt and the like including a salt with a mineral acid, for example, hydrochloric acid salt, hydrobromic acid salt, hydroiodic acid salt, sulfuric acid salt, nitric acid salt, phosphoric acid salt and the like; an organic acid addition salt, for example, benzoic acid salt, methanesulfonic acid salt, ethanesulfonic acid salt, benzene sulfonic acid salt, p-toluene sulfonic acid salt, maleic acid salt, fumaric acid salt, tartaric acid salt, citric acid salt, and acetic acid salt; or the like can be mentioned.

Examples of the solvate of the compound represented by the formula (I) or salt thereof include a hydrate and the like, but not limited thereto.

In addition, compounds which are metabolized in a living body and converted into the compounds represented by the aforementioned formula (I), so called prodrugs, all fall within the scope of the compounds of the invention. Examples of groups which form the prodrugs of the compounds of the invention include the groups described in "Progress in Medicine", vol. 5, pp. 2157-2161, 1985, Life Science Medica, and the groups described in "Development of Drugs", vol. 7, Molecular Designs, pp. 163 to 198, 1990, Hirokawa Shoten.

The compounds represented by the formula (I), or salts or solvates thereof can be produced according to various known methods, and the production method is not specifically limited. For example, the compounds can be produced according to the following reaction step. Further, when each reaction shown below is performed, functional groups other than the reaction sites may be protected beforehand as required, and deprotected in an appropriate stage. Furthermore, the reaction in each step may be performed by an ordinarily used method, and isolation and purification can be performed by a method suitably selected from conventional methods such as crystallization, recrystallization, chromatography, or the like, or a combination thereof.

(Production Method)

1. Method for Production of the Compound (Ia) Wherein Ring B is Formula (IV)

Among the compounds represented by the formula (I) of the invention, the compounds represented by the formula (Ia) can be produced according to the following method, but the production method is not limited thereto.

Specifically, as illustrated in the Reaction Scheme 1 below, pyridinylmethyl halide represented by the formula (VI) is reacted with β-ketoester represented by the formula (VII), the resulting compound represented by the formula (VIII) is reacted with ammonium acetate, and subsequently reacted with acid anhydride represented by the formula (IX) or acid chloride represented by the formula (X) to give an acylamino compound represented by the formula (XI). The acylamino compound represented by the formula (XI) is reacted with an amino compound represented by the formula (XII) to give a pyrimidinone derivative represented by the formula (XIII). The pyrimidinone derivative represented by the formula (XIII) is reacted with an azide compound to produce the compounds represented by the formula (Ia) of the present invention.

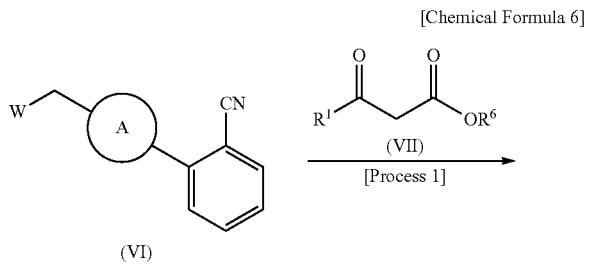

[Chemical Formula 6]

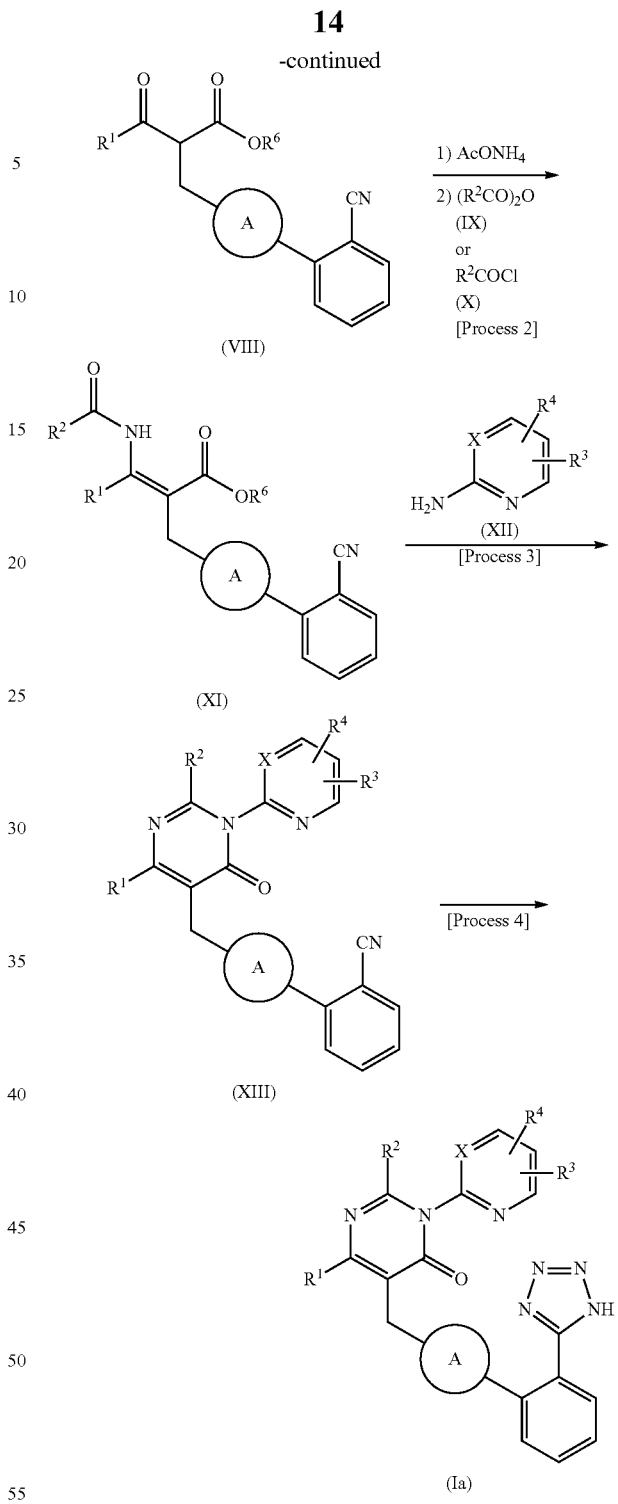

(in the formula, Ring A, $R^1$, $R^2$, $R^3$, $R^4$, and X are as defined above, $R^6$ represents a protecting group for the carboxyl group of a $C_{1-6}$ alkyl group and the like, and W represents a leaving group such as a halogen atom.)

[Process 1]

The reaction between the pyridinylmethyl halide (VI) and β-ketoester (VII) may be carried out in a solvent in the presence of a base and lithium chloride. The solvent is not specifically limited, and N,N-dimethylformamide, N-methylpyrrolidone, dimethyl sulfoxide, dioxane, tetrahydrofuran, acetonitrile, propionitrile, and the like may be used either alone or in combination thereof. The base is not particularly limited, and the examples thereof include organic bases such as pyridine, N,N-dimethylaminopyridine (DMAP), collidine, lutidine, 1,8-diazabicyclo[5.4.0]-7-undecene (DBU), 1,5-diazabicyclo[4.3.0]-5-nonene (DBN), 1,4-diazabicyclo[2.2.2]octane (DABCO), triethylamine, diisopropylamine, diisopropylethylamine, diisopropylpentylamine, and trimethylamine, alkali metal hydrides such as lithium hydride, sodium hydride, and potassium hydride, alkali metal hydroxides such as lithium hydroxide, sodium hydroxide, and potassium hydroxide, alkali metal carbonates such as lithium carbonate, sodium carbonate, potassium carbonate, and cesium carbonate, and alkali metal bicarbonates such as sodium hydrogen carbonate. The reaction conditions may vary depending on the reaction materials used. However, the reaction is generally carried out at −20 to 120° C., preferably 20 C to 100° C. for 1 minute to 2 days, and more preferably 5 minutes to 36 hours to obtain the compound (VIII).

[Process 2-1]

The reaction between the compound (VIII) and ammonium acetate may be carried out in a solvent in the presence of an acid. The solvent is not specifically limited, and methanol, ethanol, isopropanol, ethyl acetate, isopropyl acetate, toluene, benzene, dioxane, tetrahydrofuran, acetonitrile, propionitrile, N,N-dimethylformamide, N-methylpyrrolidone, dimethyl sulfoxide, and the like may be used either alone or in combination thereof. The acid is not particularly limited, and the examples thereof include a protonic acid like acetic acid, trifluoroacetic acid, propionic acid, benzoic acid, and the like and Lewis acid like titanium tetrachloride, boron trifluoride, stannic chloride, and the like. The reaction conditions may vary depending on the reaction materials used. However, the reaction is generally carried out at 0 to 180° C., preferably 50° C. to 150° C. for 1 minute to 24 hours, and more preferably 5 minutes to 18 hours.

[Process 2-2]

The reaction between the crude product obtained by distilling the solvent away and acid anhydride (IX) may be carried out in the presence of an acid. The acid is not particularly limited, and examples thereof include a protonic acid like acetic acid, trifluoroacetic acid, propionic acid, benzoic acid, and the like. The reaction conditions may vary depending on the reaction materials used. However, the reaction is generally carried out at 0 to 180° C., preferably 50° C. to 120° C. for 1 minute to 2 days, and more preferably 5 minutes to 24 hours to obtain the acylamino compound (XI).

In addition, the reaction between the crude product obtained by distilling the solvent away and acid chloride (X) may be carried out in a solvent, in the presence or in the absence of a base. The solvent is not specifically limited, and tetrahydrofuran, toluene, dioxane, N,N-dimethylformamide, N-methylpyrrolidone, 1,2-dichloroethane, dichloromethane, chloroform, acetonitrile, propionitrile, and the like may be used either alone or in combination thereof. The base is not particularly limited, and the examples thereof include organic bases like pyridine, DMAP, collidine, lutidine, DBU, DBN, DABCO, triethylamine, diisopropylamine, diisopropylethylamine, diisopropylpentylamine, trimethylamine, and the like, alkali metal hydrides like lithium hydride, sodium hydride, potassium hydride, and the like, alkali metal hydroxides like lithium hydroxide, sodium hydroxide, potassium hydroxide, and the like, alkali metal carbonates like lithium carbonate, sodium carbonate, potassium carbonate, cesium carbonate, and the like, sodium hydrocarbonate, and the like. The reaction conditions may vary depending on the reaction materials used. However, the reaction is carried out generally at −20 to 100° C., preferably 15 to 80° C. for 5 minutes to 48 hours, and preferably 5 hours to 36 hours to obtain the acylamino compound (XI).

[Process 3]

The reaction between the acylamino compound (XI) obtained in the method described above and the amino compound (XII) may be carried out in a solvent, in the presence of trialkylaluminum. The solvent is not specifically limited, and 1,2-dichloroethane, chloroform, dichloromethane, ethyl acetate, isopropyl acetate, toluene, benzene, tetrahydrofuran, dioxane, acetonitrile, propionitrile, hexane, and the like may be used either alone or in combination thereof. As the trialkylaluminum, the examples thereof include trimethylaluminum, triethylaluminum, tripropylaluminum, and the like. The reaction conditions may vary depending on the reaction materials used. However, the reaction is carried out generally at 0 to 150° C., preferably at 50° C. to 120° C. for 1 minute to 24 hours, and more preferably 5 minutes to 20 hours to obtain the pyrimidinone derivative (VIII).

[Process 4]

The reaction between the pyrimidinone derivative (XIII) and an azide compound may be carried out in a solvent. As the azide compound, the examples thereof include trimethyltin azide, tributyltin azide, triphenyltin azide, sodium azide, hydrazoic acid, and the like. Furthermore, trimethylsilyl azide may be used in the presence of dibutyltin oxide. The solvent is not specifically limited, and methanol, ethanol, isopropanol, ethyl acetate, isopropyl acetate, toluene, benzene, dioxane, tetrahydrofuran, acetonitrile, propionitrile, N,N-dimethylformamide, N-methylpyrrolidone, dimethyl sulfoxide, and the like may be used either alone or in combination thereof. The reaction conditions may vary depending on the reaction materials used. However, the reaction is carried out generally at 0 to 180° C., preferably at 50° C. to 120° C. for 1 minute to 2 weeks, and more preferably 1 hour to 3 days to obtain the target compound.

2. Method for Production of the Compound (Ib) Wherein Ring B is Formula (V)

Among the compounds represented by the formula (I) of the invention, the compounds represented by the formula (Ib) can be produced according to the following method, but the production method is not limited thereto.

Specifically, as illustrated in the Reaction Scheme 2 below, a pyrimidinone derivative represented by the formula (XIII) is reacted with hydroxylamine to give an amide oxime represented by the formula (XIV). The amide oxime represented by the formula (XIV) is reacted with a carbonylation reagent to produce the compounds represented by the formula (Ib) of the present invention.

[Reaction Scheme 2]

[Chemical Formula 7]

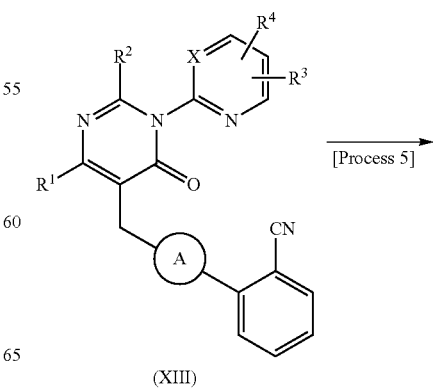

[Process 5]

(XIII)

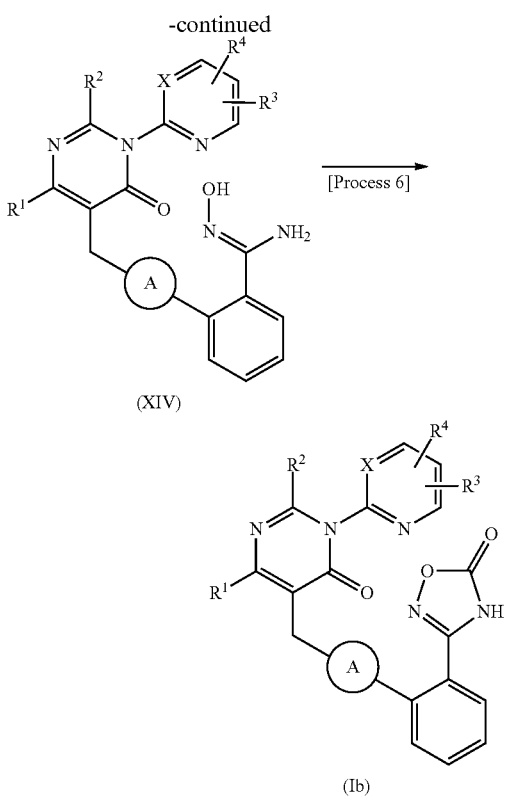

(in the formula, Ring A, $R^1$, $R^2$, $R^3$, $R^4$ and X are as defined above.)

[Process 5]

The reaction between the pyrimidinone derivative (XIII) and hydroxyl amine may be carried out in a solvent. The solvent is not specifically limited, and N,N-dimethylformamide, N,N-dimethylacetamide, N-methylpyrrolidone, dimethyl sulfoxide, methanol, ethanol, isopropanol, 1,4-dioxane, tetrahydrofuran, and the like may be used either alone or in combination thereof. When a salt with an acid such as hydroxyl amine hydrochloride, hydroxyl amine sulfate, and hydroxyl amine oxalate is used as the hydroxyl amine, the reaction may be carried out in the coexistence of an equivalent amount or a bit excessive amount of an appropriate base, for example, potassium carbonate, sodium hydrogen carbonate, sodium hydroxide, triethylamine, sodium methoxide, sodium hydride, and the like. The reaction conditions may vary depending on the reaction materials used. However, the reaction is generally carried out at 0 to 180° C., and preferably 50 to 120° C., for 1 minute to 3 days, and preferably 1 hour to 36 hours to obtain the amide oxime (XIV).

[Process 6]

The conversion from the amide oxime (XIV) to the compound (Ib) may be carried out in a solvent in the presence of a base using a carbonylation reagent. The solvent is not specifically limited, and 1,2-dichloroethane, chloroform, dichloromethane, ethyl acetate, isopropyl acetate, toluene, benzene, tetrahydrofuran, dioxane, acetonitrile, propionitrile, N,N-dimethylformamide, N,N-dimethylacetamide, N-methylpyrrolidone, diethyl ether, and the like may be used either alone or in combination thereof. The base is not specifically limited, and the examples thereof include pyridine, DMAP, collidine, lutidine, DBU, DBN, DABCO, triethylamine, diisopropylethylamine, diisopropylpentylamine, trimethylamine, lithium carbonate, sodium carbonate, potassium carbonate, cesium carbonate, sodium hydrogen carbonate, potassium hydrogen carbonate, and the like. The carbonylation reagent is not specifically limited, and 1,1'-carbonyl diimidazole, triphosgene, methyl chlorocarbonate, ethyl chlorocarbonate and the like may be used. The reaction conditions may vary depending on the reaction materials used. However, the reaction is generally carried out at 0 to 120° C., preferably 15 to 80° C. for 5 minutes to 3 days, and more preferably 1 hour to 12 hours to obtain the compound (Ib).

If necessary, the intermediates and target compounds that are obtained from each of the reaction above can be isolated and purified by a purification method that is generally used in a field of organic synthesis chemistry, e.g., filtration, extraction, washing, drying, concentration, recrystallization, various chromatographic methods, and the like. Furthermore, the intermediates may be used for the next reaction without any specific purification.

Various isomers may be isolated by applying a general method based on a difference in physicochemical properties among the isomers. For example, a racemic mixture may be resolved into an optically pure isomer by common racemic resolution like optical resolution by which a diastereomer salt is formed with a common optically active acid like tartaric acid or a method of using optically active chromatography. Further, a mixture of diastereomers can be resolved by fractional crystallization or various chromatographic methods, for example. Furthermore, an optically active compound can be also produced by using an appropriate starting compound that is optically active.

The compound (I) obtained may be converted into a salt according to a common method. Furthermore, it may be converted into a solvate with a solvent like a solvent for reaction or a solvent for recrystallization, or into a hydrate.

Examples of a dosage form of the pharmaceutical composition containing the compounds of the invention, salts or solvates thereof as an effective component include, for example, those for oral administration such as tablet, capsule, granule, powder, syrup, or the like and those for parenteral administration such as intravenous injection, intramuscular injection, suppository, inhalant, transdermal preparation, eye drop, nasal drop, or the like. In order to prepare a pharmaceutical preparation in the various dosage forms, the effective component may be used alone, or may be used in appropriate combination with other pharmaceutically acceptable carriers such as excipients, binders, extending agents, disintegrating agents, surfactants, lubricants, dispersing agents, buffering agents, preservatives, corrigents, perfumes, coating agents, diluents, and the like to give a pharmaceutical composition.

Although the administration amount of the pharmaceutical agent of the invention may vary depending on the weight, age, sex, symptoms, and the like of a patient, in terms of the compound represented by the general formula (I), generally 0.1 to 1000 mg, especially 1 to 300 mg, may be administered orally or parenterally at one time or several times as divided portions per day for an adult.

EXAMPLES

Hereinbelow, the invention will be explained in greater detail with reference to examples. However, the invention is not limited to these examples. The abbreviations used in the examples have the following meanings.

s: singlet
d: doublet
t: triplet
q: quartet
m: multiplet br: broad
J: coupling constant
Hz: hertz
CDCl$_3$: deuterated chloroform
DMSO-d$_6$: deuterated dimethyl sulfoxide
$^1$H-NMR: proton nuclear magnetic resonance
IR: infrared absorption spectrum Example 1

Production of 5-{{6-[2-(1H-tetrazol-5-yl)phenyl]pyridin-3-yl}methyl}-6-butyl-3-(5-methoxypyrimidin-2-yl)-2-methylpyrimidin-4(3H)-one

[Chemical Formula 8]

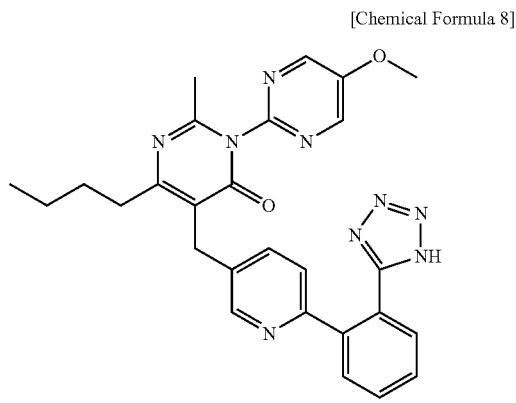 [SMILES: CCCCc1nc(C)n(-c2ncc(OC)cn2)c(=O)c1Cc1ccc(-c2ccccc2-c2nnn[nH]2)nc1]

Process 1: Under argon atmosphere, a tetrahydrofuran (900 mL) solution of 2-[5-(bromomethyl)pyridin-2-yl]benzonitrile (31.9 g, 117 mmol), methyl 3-oxoheptanoate (27.8 g, 176 mmol), diisopropylethylamine (31.0 g, 240 mmol), and lithium chloride (8.2 g, 193 mmol) was refluxed for 23 hours under heating. The reaction mixture was added water and extracted with ethyl acetate. The organic layer was combined, washed with water and brine, dried over anhydeous sodium sulfate, and concentrated in vacuo. The residues obtained were subjected to silica gel column chromatography (hexane/ethyl acetate=2:1), to obtain methyl 2-{[6-(2-cyanophenyl)pyridin-3-yl]methyl}-3-oxoheptanoate (20.9 g, 51%) as a brown oil.

$^1$H-NMR (CDCl$_3$) δ:
0.87 (3H, t, J=7 Hz), 1.18-1.32 (2H, m), 1.47-1.59 (2H, m), 2.34-2.39 (1H, m), 2.55-2.67 (1H, m), 3.20-3.29 (2H, m), 3.73 (3H, s), 3.84 (1H, t, J=7 Hz), 7.50 (1H, td, J=8, 1 Hz), 7.63-7.74 (3H, m), 7.76-7.87 (2H, m), 8.61 (1H, s).

Process 2: A toluene (50 mL)-acetic acid (7 mL) solution of methyl 2-{[6-(2-cyanophenyl)pyridin-3-yl]methyl}-3-oxoheptanoate (3.50 g, 10.0 mmol) and ammonium acetate (23.2 g, 300 mmol) was refluxed for 1 hour under heating. The solvent was distilled off and the residues were added anhydrous acetic acid (51.2 g) and acetic acid (5.7 g) under room temperature, and the reaction solution was stirred at 0° C. for 30 minutes, and then stirred at 70° C. for 1.5 hours. The reaction solution was added aqueous sodium bicarbonate, and extracted with chloroform. The organic layer was combined, washed with brine, dried over anhydrous sodium sulfate, and concentrated in vacuo. The residues obtained were subjected to silica gel column chromatography (hexane/acetone=5:1), to obtain methyl(Z)-3-acetamido-2-{[6-(2-cyanophenyl)pyridin-3-yl]methyl}-2-heptenoate (0.975 g, 25%) as a pale yellow oil.

$^1$H-NMR (CDCl$_3$) δ:
0.91 (3H, t, J=7 Hz), 1.33-1.45 (2H, m), 1.46-1.57 (2H, m), 2.18 (3H, s), 2.94 (2H, t, J=6 Hz), 3.71 (3H, s), 3.75 (2H, s), 7.50 (1H, t, J=8 Hz), 7.58 (1H, d, J=8 Hz), 7.63-7.72 (2H, m), 7.75-7.83 (2H, m), 8.60 (1H, s), 11.9 (1H, s).

Process 3: Under argon atmosphere, trimethylaluminum (2 mol/L hexane solution, 1.45 mL, 2.90 mmol) was added to 1,2-dichloroethane (30 mL) solution of 2-amino-5-methoxypyrimidine (220 mg, 1.74 mmol) at room temperature, and stirred at the same temperature for 80 minutes. 1,2-dichloroethane (20 mL) solution of methyl(Z)-3-acetamido-2-{[6-(2-cyanophenyl)pyridin-3-yl]methyl}-2-heptenoate (227 mg, 0.58 mmol) was added dropwise thereto at room temperature followed by reflux for 17 hours under heating. An aqueous solution of ammonium chloride and chloroform were added to the reaction mixture, which was then filtered through a pad of celite. The organic layer in the filtrate was separated, and the aqueous layer was extracted with chloroform. The organic layer was combined, washed with water and brine, dried over anhydrous sodium sulfate, and concentrated in vacuo. The residues obtained were subjected to silica gel column chromatography (hexane/ethyl acetate=2:1) to obtain 2-{5-{[4-butyl-1-(5-methoxypyrimidin-2-yl)-2-methyl-6-oxo-1,6-dihydropyrimidin-5-yl]methyl}pyridin-2-yl}benzonitrile (207 mg, 77%) as a yellow oil.

$^1$H-NMR (CDCl$_3$) δ:
0.95 (3H, t, J=7 Hz), 1.36-1.48 (2H, m), 1.58-1.70 (2H, m), 2.16 (3H, s), 2.63-2.72 (2H, m), 3.97 (2H, s), 4.01 (2H, s), 7.47 (1H, m), 7.60-7.71 (2H, m), 7.72-7.83 (3H, m), 8.54 (2H, s), 8.70 (1H, d, J=1 Hz).

Process 4: Trimethylsilyl azide (8.68 g, 75.3 mmol) and dibutyl tin oxide (55 mg, 0.221 mmol) were added to toluene (20 mL) solution of 2-{5-{[4-butyl-1-(5-methoxypyrimidin-2-yl)-2-methyl-6-oxo-1,6-dihydropyrimidin-5-yl]methyl}pyridin-2-yl}benzonitrile (200 mg, 0.43 mmol), and stirred under argon atmosphere at 95° C. for 24 hours. The reaction solvent was distilled off, and the residue obtained was isolated and purified by silica gel column chromatography (chloroform:methanol=100:1), to obtain 5-{{6-[2-(1H-tetrazol-5-yl)phenyl]pyridin-3-yl}methyl}-6-butyl-3-(5-methoxypyrimidin-2-yl)-2-methylpyrimidin-4(3H)-one (174 mg, 80%) as a yellow oil.

$^1$H-NMR (CDCl$_3$) δ:
0.93 (3H, t, J=7 Hz), 1.33-1.48 (2H, m), 1.55-1.73 (2H, m), 2.16 (3H, s), 2.58-2.72 (2H, m), 3.95 (2H, s), 4.00 (3H, s), 7.20-7.35 (1H, m), 7.38-7.58 (3H, m), 7.62-7.82 (1H, m), 8.00-8.22 (1H, m), 8.54 (2H, s), 8.50-8.63 (1H, m).

Example 2

Production of 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one

[Chemical Formula 9]

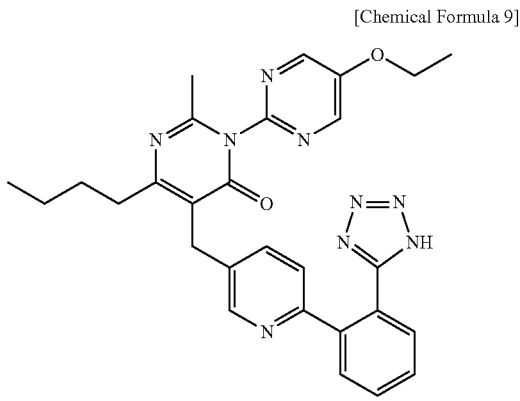 [SMILES: CCCCc1nc(C)n(-c2ncc(OCC)cn2)c(=O)c1Cc1ccc(-c2ccccc2-c2nnn[nH]2)nc1]

Process 1:
2-{5-{[4-butyl-1-(5-ethoxypyrimidin-2-yl)-2-methyl-6-oxo-1,6-dihydropyrimidin-5-yl]methyl}pyridin-2- yl}benzonitrile (yield: 46%) was obtained according to the same reaction and treatment as the Process 3 of Example 1 by using 2-amino-5-ethoxypyrimidine instead of the 2-amino-5-methoxypyrimidine in the Process 3 of Example 1.

$^1$H-NMR (CDCl$_3$) δ:

0.94 (3H, t, J=7 Hz), 1.38-1.46 (2H, m), 1.51 (3H, t, J=7 Hz), 1.60-1.68 (2H, m), 2.16 (3H, s), 2.65-2.69 (2H, m), 3.97 (2H, s), 4.22 (2H, q, J=7 Hz), 7.47 (1H, m), 7.64-7.81 (5H, m), 8.51 (2H, s), 8.70 (1H, d, J=1 Hz).

Process 2: 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one (yield: 46%) was obtained as a pale yellow amorphous according to the same reaction and treatment as the Process 4 of Example 1 by using 2-{5-{[4-butyl-1-(5-ethoxypyrimidin-2-yl)-2-methyl-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.94 (3H, t, J=7 Hz), 1.38-1.44 (2H, m), 1.51 (3H, t, J=7 Hz), 1.61-1.68 (2H, m), 2.17 (3H, s), 2.66-2.70 (2H, m), 3.97 (2H, s), 4.22 (2H, q, J=7 Hz), 7.37 (1H, m), 7.48-7.58 (3H, m), 7.78 (1H, m), 8.21 (1H, m), 8.51 (2H, s), 8.62 (1H, m).

Example 3

Production of 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one

[Chemical Formula 10]

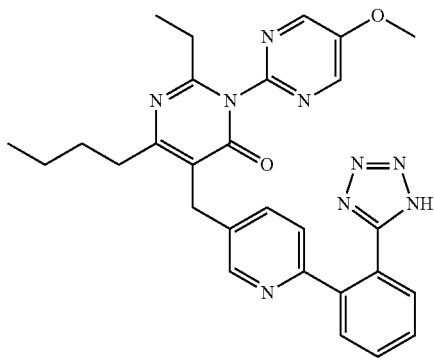

Process 1: Toluene (36 mL)-acetic acid (4 mL) solution of methyl 2-{[6-(2-cyanophenyl)pyridin-3-yl]methyl}-3-oxoheptanoate (1.03 g, 2.94 mmol) obtained in the Process 1 of Example 1 and ammonium acetate (6.80 g, 88.2 mmol) was refluxed for 1 hour under heating. The solvent was distilled off and the resulting residues were added water and an aqueous solution of 2 mol/L sodium hydroxide, and extracted with chloroform. The solvent was distilled off and then a solution of the resulting residue in 1,2-dichloroethane (10 mL) was added propionyl chloride (544 mg, 5.88 mmol) and triethylamine (595 mg, 5.88 mmol), and stirred at 50° C. for 16 hours. The reaction solution was added water, and extracted with chloroform. The organic layer was combined, washed with brine, dried over anhydrous sodium sulfate, and concentrated in vacuo. The residues obtained were subjected to silica gel column chromatography (hexane/acetone=5:1), to obtain methyl(Z)-2-{[6-(2-cyanophenyl)pyridin-3-yl]methyl}-3-propionamido-2-heptenoate (464 mg, 39%) as a brown oil.

$^1$H-NMR (CDCl$_3$) δ:

0.91 (3H, t, J=7 Hz), 1.23 (3H, t, J=8 Hz), 1.34-1.51 (4H, m), 2.43 (2H, q, J=8 Hz), 2.89-2.99 (2H, m), 3.70 (3H, s), 3.75 (2H, s), 7.49 (1H, td, J=8, 1 Hz), 7.58 (1H, dd, J=8, 2 Hz), 7.64-7.73 (2H, m), 7.77-7.86 (2H, m), 8.60 (1H, s), 11.88 (1H, s).

Process 2: 2-{5-{[4-butyl-2-ethyl-1-(5-methoxypyrimidin-2-yl)-6-oxo-1,6-dihydropyrimidin-5-yl]methyl}pyridin-2-yl}benzonitrile (yield: 70%) was obtained as a pale yellow solid according to the same reaction and treatment as the Process 3 of Example 1 by using methyl(Z)-2-{[6-(2-cyanophenyl)pyridin-3-yl]methyl}-3-propionamido-2-heptenoate instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.94 (3H, t, J=7 Hz), 1.18 (3H, t, J=7 Hz), 1.35-1.46 (2H, m), 1.62-1.74 (2H, m), 2.32 (2H, q, J=7 Hz), 2.69 (2H, t, J=8 Hz), 3.96 (2H, s), 4.00 (3H, s), 7.47 (1H, td, J=8, 1 Hz), 7.61-7.70 (2H, m), 7.73-7.82 (3H, m), 8.53 (2H, s), 8.69 (1H, s).

Process 3: 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one (yield: 60%) was obtained as a colorless viscous oil according to the same reaction and treatment as the Process 4 of Example by using 2-{5-{[4-butyl-2-ethyl-1-(5-methoxypyrimidin-2-yl)-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.94 (3H, t, J=7 Hz), 1.18 (3H, t, J=7 Hz), 1.34-1.47 (2H, m), 1.60-1.75 (2H, m), 2.32 (2H, q, J=7 Hz), 2.70 (2H, t, J=8 Hz), 3.96 (2H, s), 4.01 (3H, s), 7.29-7.38 (1H, m), 7.43-7.59 (3H, m), 7.76 (1H, d, J=8 Hz), 8.18 (1H, s), 8.54 (2H, s), 8.61 (1H, br s).

Example 4

Production of 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one

[Chemical Formula 11]

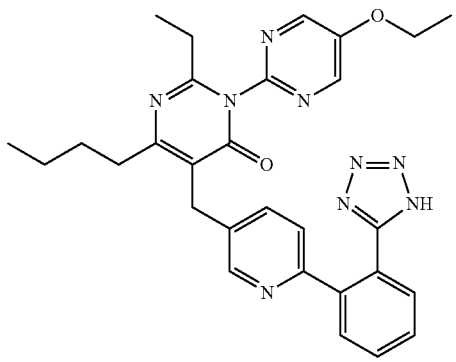

Process 1: 2-{5-{[4-butyl-1-(5-ethoxypyrimidin-2-yl)-2-ethyl-6-oxo-1,6-dihydropyrimidin-5-yl]methyl}pyridin-2- yl}benzonitrile (yield: 80%) was obtained as a pale yellow solid according to the same reaction and treatment as the Process 2 of Example 3 by using 2-amino-5-ethoxypyrimidine instead of the 2-amino-5-methoxypyrimidine in the Process 2 of Example 3.

$^1$H-NMR (CDCl$_3$) δ:

0.94 (3H, t, J=7 Hz), 1.18 (3H, t, J=7 Hz), 1.37-1.47 (2H, m), 1.51 (3H, t, J=7 Hz), 1.62-1.72 (2H, m), 2.32 (2H, q, J=7 Hz), 2.66-2.72 (2H, m), 3.97 (2H, s), 4.22 (2H, q, J=7 Hz), 7.47 (1H, t, J=8 Hz), 7.64-7.69 (2H, m), 7.74-7.83 (3H, m), 8.51 (2H, s), 8.70 (1H, d, J=2 Hz).

Process 2: 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one (yield: 75%) was obtained as a colorless viscous oil according to the same reaction and treatment as the Process 4 of Example 1 by using 2-{5-{[4-butyl-1-(5-ethoxypyrimidin-2-yl)-2-ethyl-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.94 (3H, t, J=7 Hz), 1.18 (3H, t, J=7 Hz), 1.36-1.47 (2H, m), 1.51 (3H, t, J=7 Hz), 1.61-1.74 (2H, m), 2.33 (2H, q, J=7 Hz), 2.70 (2H, t, J=8 Hz), 3.97 (2H, s), 4.22 (2H, q, J=7 Hz), 7.38 (1H, d, J=8 Hz), 7.47-7.60 (3H, m), 7.78 (1H, dd, J=8, 2 Hz), 8.20-8.28 (1H, m), 8.51 (2H, s), 8.64 (1H, s).

Example 5

Production of 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one

[Chemical Formula 12]

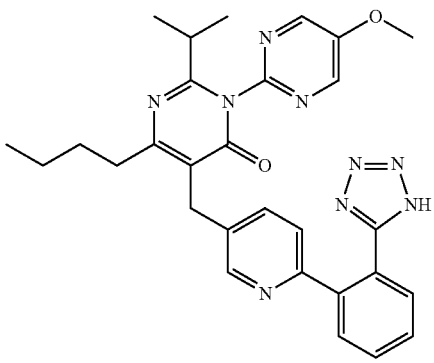

Process 1: Methyl(Z)-2-{[6-(2-cyanophenyl)pyridin-3-yl]methyl}-3-isobutylamido-2-heptenoate (yield: 49%) was obtained as a brown oil according to the same reaction and treatment as the Process 1 of Example 3 by using the isobutyryl chloride instead of the propionyl chloride in the Process 1 of Example 3.

$^1$H-NMR (CDCl$_3$) δ:

0.90 (3H, t, J=7 Hz), 1.25 (6H, d, J=7 Hz), 1.33-1.55 (4H, m), 2.49-2.63 (1H, m), 2.90-2.99 (2H, m), 3.71 (3H, s), 3.75 (2H, s), 7.49 (1H, td, J=8, 1 Hz), 7.59 (1H, dd, J=8, 2 Hz), 7.64-7.73 (2H, m), 7.79 (1H, dd, J=8, 1 Hz), 7.83 (1H, dd, J=8, 1 Hz), 8.61 (1H, d, J=1 Hz), 11.90 (1H, s).

Process 2: 2-{5-{[4-butyl-2-isopropyl-1-(5-methoxypyrimidin-2-yl)-6-oxo-1,6-dihydropyrimidin-5-yl]methyl}pyridin-2-yl}benzonitrile (yield: 55%) was obtained as a yellow oil according to the same reaction and treatment as the Process 3 of Example 1 by using methyl(Z)-2-{[6-(2-cyanophenyl)pyridin-3-yl]methyl}-3-isobutylamido-2-heptenoate instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.94 (3H, t, J=7 Hz), 1.20 (6H, d, J=7 Hz), 1.33-1.49 (2H, m), 1.62-1.75 (2H, m), 2.21-2.35 (1H, m), 2.69 (2H, t, J=8 Hz), 3.95 (2H, s), 4.00 (3H, s), 7.46 (1H, td, J=8, 1 Hz), 7.61-7.70 (2H, m), 7.74-7.83 (3H, m), 8.53 (2H, s), 8.69 (1H, d, J=1 Hz).

Process 3: 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one (yield: 69%) was obtained as a colorless viscous oil according to the same reaction and treatment as the Process 4 of Example 1 by using 2-{5-{[4-butyl-2-isopropyl-1-(5-methoxypyrimidin-2-yl)-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.94 (3H, t, J=7 Hz), 1.20 (6H, d, J=7 Hz), 1.33-1.47 (2H, m), 1.60-1.75 (2H, m), 2.22-2.35 (1H, m), 2.70 (2H, t, J=8 Hz), 3.95 (2H, s), 4.01 (3H, s), 7.33 (1H, d, J=8 Hz), 7.45-7.57 (3H, m), 7.77 (1H, d, J=7 Hz), 8.18 (1H, br s), 8.53 (2H, s), 8.61 (1H, s).

Example 6

Production of 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one

[Chemical Formula 13]

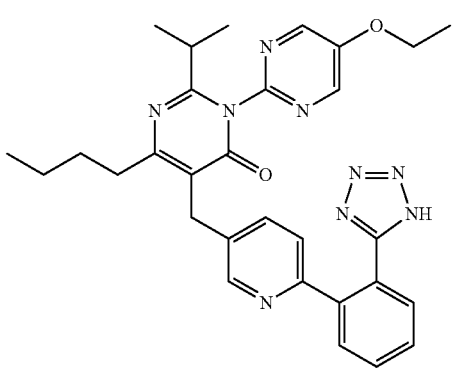

Process 1: 2-{5-{[4-butyl-1-(5-ethoxypyrimidin-2-yl)-2-isopropyl-6-oxo-1,6-dihydropyrimidin-5-yl]methyl}pyridin-2-yl}benzonitrile (yield: 79%) was obtained as a pale yellow solid according to the same reaction and treatment as the Process 3 of Example 1 by using the methyl (Z)-2-{[6-(2-cyanophenyl)pyridin-3-yl]methyl}-3-isobutylamido-2-heptenoate obtained in the Process 1 of Example 5 instead of the methyl(Z)-3-acetamido-2-{[6-(2-cyanophenyl)pyridin-3-yl]methyl}-2-heptenoate and 2-amino-5- ethoxypyrimidine instead of the 2-amino-5-methoxypyrimidine in the Process 3 of Example 1.

$^1$H-NMR (CDCl$_3$) δ:
0.94 (3H, t, J=7 Hz), 1.19 (6H, d, J=7 Hz), 1.35-1.45 (2H, m), 1.51 (3H, t, J=7 Hz), 1.63-1.74 (2H, m), 2.22-2.35 (1H, m), 2.69 (2H, t, J=8 Hz), 3.95 (2H, s), 4.22 (2H, q, J=7 Hz), 7.46 (1H, td, J=8, 1 Hz), 7.62-7.70 (2H, m), 7.75-7.83 (3H, m), 8.50 (2H, s), 8.67-8.71 (1H, m).

Process 2: 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one (yield: 99%) was obtained as a pale brown viscous oil according to the same reaction and treatment as the Process 4 of Example 1 by using 2-{5-{[4-butyl-1-(5-ethoxypyrimidin-2-yl)-2-isopropyl-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:
0.94 (3H, t, J=7 Hz), 1.20 (6H, d, J=7 Hz), 1.35-1.46 (2H, m), 1.51 (3H, t, J=7 Hz), 1.63-1.75 (2H, m), 2.22-2.35 (1H, m), 2.71 (2H, t, J=7 Hz), 3.96 (2H, s), 4.22 (2H, q, J=7 Hz), 7.37-7.45 (1H, m), 7.48-7.63 (3H, m), 7.81 (1H, dd, J=8, 2 Hz), 8.25-8.33 (1H, m), 8.51 (2H, s), 8.67 (1H, s).

Example 7

Production of 5-{{6-[2-(1H-tetrazol-5-yl)phenyl] pyridin-3-yl}methyl}-6-butyl-2-cyclopropyl-3-(5-methoxypyrimidin-2-yl)pyrimidin-4(3H)-one

[Chemical Formula 14]

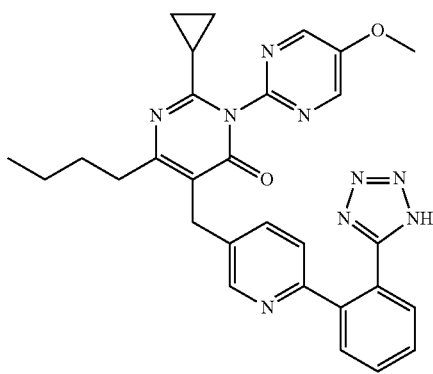

Process 1: Methyl(Z)-2-{[6-(2-cyanophenyl)pyridin-3-yl]methyl}-3-(cyclopropane carboxamide)-2-heptenoate (yield: 69%) was obtained as a yellow oil according to the same reaction and treatment as the Process 1 of Example 3 by using cyclopropane carbonyl chloride instead of the propionyl chloride in the Process 1 of Example 3.

$^1$H-NMR (CDCl$_3$) δ:
0.78-0.98 (5H, m), 1.02-1.12 (2H, m), 1.31-1.65 (5H, m), 2.88-3.02 (2H, m), 3.72 (3H, s), 3.76 (2H, s), 7.50 (1H, t, J=8 Hz), 7.60 (1H, d, J=8 Hz), 7.63-7.74 (2H, m), 7.76-7.87 (2H, m), 8.61 (1H, s), 12.2 (1H, s).

Process 2: 2-{5-{[4-butyl-2-cyclopropyl-1-(5-methoxypyrimidin-2-yl)-6-oxo-1,6-dihydropyrimidin-5-yl]methyl}pyridin-2-yl}benzonitrile (yield: 63%) was obtained as a yellow oil according to the same reaction and treatment as the Process 3 of Example 1 by using methyl(Z)-2-{[6-(2-cyanophenyl)pyridin-3-yl]methyl}-3-(cyclopropane carboxamide)-2-heptenoate instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:
0.82-0.87 (2H, m), 0.92 (3H, t, J=7 Hz), 1.07-1.15 (1H, m), 1.21-1.27 (2H, m), 1.32-1.41 (2H, m), 1.53-1.64 (2H, m), 2.61 (2H, t, J=8 Hz), 3.94 (2H, s), 4.01 (3H, s), 7.44-7.49 (1H, m), 7.66 (2H, t, J=8 Hz), 7.74-7.82 (3H, m), 8.56 (2H, s), 8.68 (1H, d, J=2 Hz).

Process 3: 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one (yield: 100%) was obtained as a pale yellow viscous oil according to the same reaction and treatment as the Process 4 of Example 1 by using 2-{5-{[4-butyl-2-cyclopropyl-1-(5-methoxypyrimidin-2-yl)-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:
0.82-0.89 (2H, m), 0.92 (3H, t, J=7 Hz), 1.06-1.15 (1H, m), 1.21-1.27 (2H, m), 1.31-1.43 (2H, m), 1.56-1.67 (2H, m), 2.63 (2H, t, J=8 Hz), 3.94 (2H, s), 4.01 (3H, s), 7.40 (1H, d, J=8 Hz), 7.47-7.62 (3H, m), 7.75-7.82 (1H, m), 8.23-8.32 (1H, m), 8.56 (2H, s), 8.65 (1H, s).

Example 8

Production of 5-{{6-[2-(1H-tetrazol-5-yl)phenyl] pyridin-3-yl}methyl}-6-butyl-2-cyclobutyl-3-(5-methoxypyrimidin-2-yl)pyrimidin-4(3H)-one

[Chemical Formula 15]

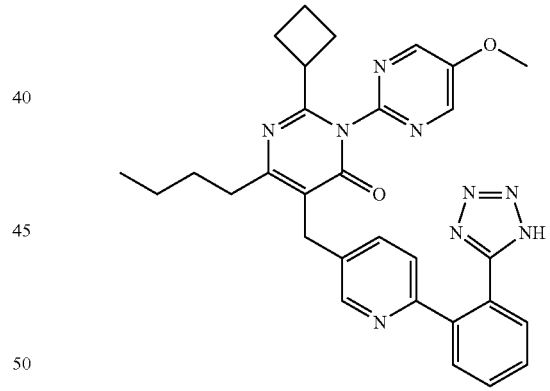

Process 1: Methyl(Z)-2-{[6-(2-cyanophenyl)pyridin-3-yl]methyl}-3-(cyclobutane carboxamide)-2-heptenoate (yield: 72%) was obtained as a brown oil according to the same reaction and treatment as the Process 1 of Example 3 by using cyclobutane carbonyl chloride instead of the propionyl chloride in the Process 1 of Example 3.

$^1$H-NMR (CDCl$_3$) δ:
0.91 (3H, t, J=7 Hz), 1.33-1.54 (4H, m), 2.19-2.44 (6H, m), 2.95 (2H, t, J=8 Hz), 3.12-3.25 (1H, m), 3.70 (3H, s), 3.75 (2H, s), 7.49 (1H, td, J=8, 1 Hz), 7.58 (1H, dd, J=8, 2 Hz), 7.64-7.73 (2H, m), 7.76-7.86 (2H, m), 8.60 (1H, s), 11.78 (1H, s).

Process 2: 2-{5-{[4-butyl-2-cyclobutyl-1-(5-methoxypyrimidin-2-yl)-6-oxo-1,6-dihydropyrimidin-5-yl]methyl}pyridin-2-yl}benzonitrile (yield: 65%) was obtained as a pale yellow solid according to the same reaction and treatment as the Process 3 of Example 1 by using methyl(Z)-2-{[6-(2-cyanophenyl)pyridin-3-yl]methyl}-3-(cyclobutane carboxamide)-2-heptenoate instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:
0.96 (3H, t, J=7 Hz), 1.34-1.51 (2H, m), 1.65-1.83 (6H, m), 2.36-2.51 (2H, m), 2.71 (2H, t, J=8 Hz), 3.07-3.17 (1H, m), 3.96 (2H, s), 4.00 (3H, s), 7.46 (1H, td, J=8, 1 Hz), 7.61-7.70 (2H, m), 7.73-7.82 (3H, m), 8.52 (2H, s), 8.69 (1H, d, J=1 Hz).

Process 3: 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one (yield: 74%) was obtained as a colorless viscous oil according to the same reaction and treatment as the Process 4 of Example 1 by using 2-{5-{[4-butyl-2-cyclobutyl-1-(5-methoxypyrimidin-2-yl)-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:
0.95 (3H, t, J=7 Hz), 1.34-1.50 (2H, m), 1.65-1.83 (6H, m), 2.37-2.51 (2H, m), 2.72 (2H, t, J=8 Hz), 3.04-3.20 (1H, m), 3.96 (2H, s), 4.01 (3H, s), 7.31 (1H, d, J=8 Hz), 7.45-7.56 (3H, m), 7.76 (1H, d, J=8 Hz), 8.16 (1H, br s), 8.52 (2H, s), 8.59 (1H, s).

Example 9

Production of 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one

[Chemical Formula 16]

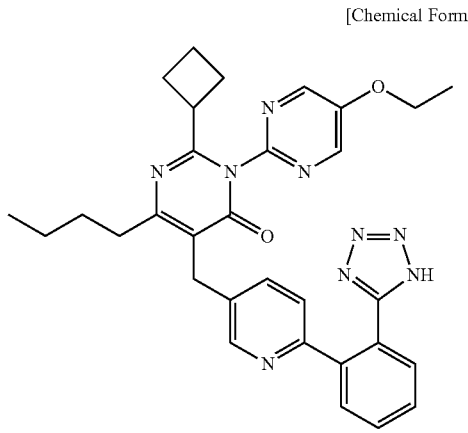

Process 1: 2-{5-{[4-butyl-2-cyclobutyl-1-(5-ethoxypyrimidin-2-yl)-6-oxo-1,6-dihydropyrimidin-5-yl]methyl}pyridin-2-yl}benzonitrile (yield: 89%) was obtained as a pale yellow solid according to the same reaction and treatment as the Process 3 of Example 1 by using methyl(Z)-2-{[6-(2-cyanophenyl)pyridin-3-yl]methyl}-3-(cyclobutane carboxamide)-2-heptenoate obtained in the Process 1 of Example 8 instead of the methyl(Z)-3-acetamido-2-{[6-(2-cyanophenyl)pyridin-3-yl]methyl}-2-heptenoate and 2-amino-5-ethoxypyrimidine instead of the 2-amino-5-methoxypyrimidine in the Process 3 of Example 1.

$^1$H-NMR (CDCl$_3$) δ:
0.96 (3H, t, J=7 Hz), 1.39-1.47 (2H, m), 1.51 (3H, t, J=7 Hz), 1.61-1.84 (6H, m), 2.36-2.51 (2H, m), 2.67-2.75 (2H, m), 3.03-3.16 (1H, m), 3.96 (2H, s), 4.22 (2H, q, J=7 Hz), 7.48 (1H, dd, J=8, 1 Hz), 7.62-7.70 (2H, m), 7.72-7.83 (3H, m), 8.49 (2H, s), 8.69 (1H, d, J=2 Hz).

Process 2: 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one (yield: 99%) was obtained as a pale brown viscous oil according to the same reaction and treatment as the Process 4 of Example 1 by using 2-{5-{[4-butyl-2-cyclobutyl-1-(5-ethoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:
0.95 (3H, t, J=7 Hz), 1.36-1.47 (2H, m), 1.51 (3H, t, J=7 Hz), 1.63-1.85 (6H, m), 2.37-2.50 (2H, m), 2.73 (2H, t, J=8 Hz), 3.07-3.18 (1H, m), 3.97 (2H, s), 4.22 (2H, q, J=7 Hz), 7.40 (1H, d, J=8 Hz), 7.48-7.62 (3H, m), 7.76-7.82 (1H, m), 8.24-8.31 (1H, m), 8.49 (2H, s), 8.66 (1H, s).

Example 10

Production of 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one

[Chemical Formula 17]

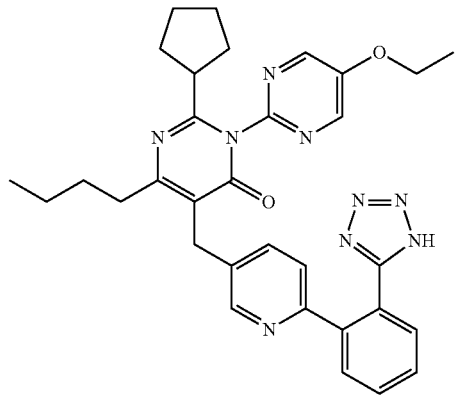

Process 1: Methyl(Z)-2-{[6-(2-cyanophenyl)pyridin-3-yl]methyl}-3-(cyclopentane carboxamide)-2-heptenoate (yield: 44%) was obtained as a brown oil according to the same reaction and treatment as the Process 1 of Example 3 by using cyclopentane carbonyl chloride instead of the propionyl chloride in the Process 1 of Example 3.

$^1$H-NMR (CDCl$_3$) δ:
0.90 (3H, t, J=7 Hz), 1.33-2.03 (12H, m), 2.70-2.82 (1H, m), 2.89-2.99 (2H, m), 3.71 (3H, s), 3.75 (2H, s), 7.49 (1H, td, J=8, 1 Hz), 7.59 (1H, dd, J=8, 2 Hz), 7.64-7.73 (2H, m), 7.76-7.86 (2H, m), 8.60 (1H, s), 11.89 (1H, s).

Process 2: 2-{5-{[4-butyl-2-cyclopentyl-1-(5-ethoxypyrimidin-2-yl)-6-oxo-1,6-dihydropyrimidin-5-yl]methyl}pyridin-2-yl}benzonitrile (yield: 57%) was obtained as a pale yellow solid according to the same reaction and treatment as the Process 3 of Example 1 by using methyl(Z)-2-{[6-(2-cyanophenyl)pyridin-3-yl]methyl}-3-(cyclopentane carboxamide)-2-heptenoate instead of the (Z)-3-acetamido-2-{[6-(2-cyanophenyl)pyridin-3-yl]methyl}-2- heptenoate and 2-amino-5-ethoxypyrimidine instead of the 2-amino-5-methoxypyrimidine in the Process 3 of Example 1.

¹H-NMR (CDCl₃) δ:
0.94 (3H, t, J=7 Hz), 1.34-1.54 (7H, m), 1.60-1.80 (6H, m), 1.90-2.03 (2H, m), 2.42-2.48 (1H, m), 2.64-2.70 (2H, m), 3.95 (2H, s), 4.22 (2H, q, J=7 Hz), 7.47 (1H, td, J=8, 1 Hz), 7.63-7.69 (2H, m), 7.77 (2H, dd, J=8, 1 Hz), 7.80 (1H, dd, J=8, 1 Hz), 8.51 (2H, s), 8.69 (1H, d, J=2 Hz).

Process 3: 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one (yield: 40%) was obtained as a pale yellow amorphous according to the same reaction and treatment as the Process 4 of Example 1 by using 2-{5-{[4-butyl-2-cyclopentyl-1-(5-ethoxypyrimidin-2-yl)-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

¹H-NMR (CDCl₃) δ:
0.94 (3H, t, J=7 Hz), 1.52 (3H, t, J=7 Hz), 1.57-1.78 (8H, m), 1.81-1.93 (5H, m), 2.70 (2H, t, J=8 Hz), 3.94 (2H, s), 4.23 (2H, q, J=7 Hz), 7.38 (1H, d, J=9 Hz), 7.47-7.62 (3H, m), 7.78 (1H, d, J=8 Hz), 8.22-8.29 (1H, m), 8.52 (2H, s), 8.65 (1H, s).

Example 11

Production of 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one

[Chemical Formula 18]

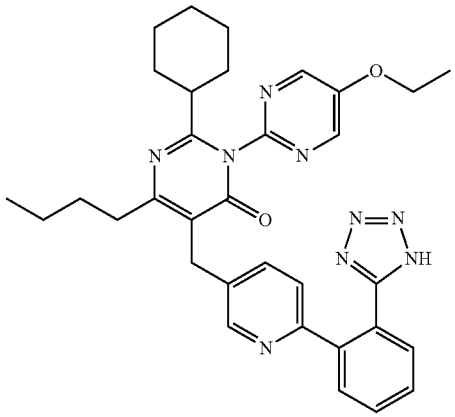

Process 1: Methyl(Z)-2-{[6-(2-cyanophenyl)pyridin-3-yl]methyl}-3-(cyclohexane carboxamide)-2-heptenoate (yield: 52%) was obtained as a brown oil according to the same reaction and treatment as the Process 1 of Example 3 by using cyclohexane carbonyl chloride instead of the propionyl chloride in the Process 1 of Example 3.

¹H-NMR (CDCl₃) δ:
0.90 (3H, t, J=7 Hz), 1.16-2.03 (14H, m), 2.45-2.59 (1H, m), 2.89-2.98 (2H, m), 3.71 (3H, s), 3.75 (2H, s), 7.49 (2H, td, J=8, 1 Hz), 7.58 (1H, dd, J=8, 2 Hz), 7.63-7.74 (2H, m), 7.76-7.86 (2H, m), 8.61 (1H, s), 11.84 (1H, br s).

Process 2: 2-{5-{[4-butyl-2-cyclohexyl-1-(5-ethoxypyrimidin-2-yl)-6-oxo-1,6-dihydropyrimidin-5-yl]methyl}pyridin-2-yl}benzonitrile (yield: 80%) was obtained as a pale yellow solid according to the same reaction and treatment as the Process 3 of Example by using methyl(Z)-2-{[6-(2-cyanophenyl)pyridin-3-yl]methyl}-3-(cyclohexane carboxamide)-2-heptenoate instead of the methyl(Z)-3-acetamido-2-{[6-(2-cyanophenyl)pyridin-3-yl]methyl}-2-heptenoate and 2-amino-5-ethoxypyrimidine instead of the 2-amino-5-methoxypyrimidine in the Process 3 of Example 1.

¹H-NMR (CDCl₃) δ:
0.94 (3H, t, J=7 Hz), 1.16-1.91 (17H, m), 2.65-2.71 (2H, m), 3.95 (2H, s), 4.23 (2H, q, J=7 Hz), 7.47 (1H, td, J=8, 1 Hz), 7.63-7.68 (2H, m), 7.75-7.82 (3H, m), 8.51 (2H, s), 8.69 (1H, d, J=1 Hz).

Process 3: 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one (yield: 58%) was obtained as a colorless viscous oil according to the same reaction and treatment as the Process 4 of Example 1 by using 2-{5-{[4-butyl-2-cyclohexyl-1-(5-ethoxypyrimidin-2-yl)-6-oxo-1,6-dihydropyrimidin-5-yl]methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

¹H-NMR (CDCl₃) δ:
0.94 (3H, t, J=7 Hz), 1.51 (3H, t, J=7 Hz), 1.61-1.82 (8H, m), 1.90-2.05 (5H, m), 2.46 (2H, t, J=8 Hz), 2.69 (2H, t, J=7 Hz), 3.95 (2H, s), 4.22 (2H, q, J=7 Hz), 7.39 (1H, d, J=8 Hz), 7.48-7.62 (3H, m), 7.79 (1H, dd, J=8, 2 Hz), 8.22-8.31 (1H, m), 8.51 (2H, s), 8.65 (1H, s).

Example 12

Production of 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one

[Chemical Formula 19]

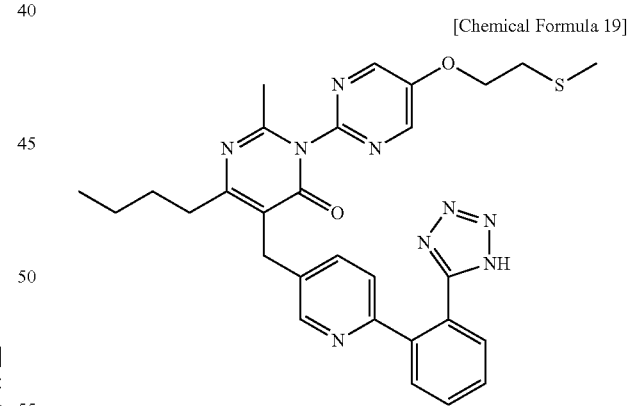

Process 1:
2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}benzonitrile (yield: 64%) was obtained as a yellow oil according to the same reaction and treatment as the Process 3 of Example 1 by using 2-amino-5-[2-(methylthio)ethoxy]pyrimidine instead of the 2-amino-5-methoxypyrimidine in the Process 3 of Example 1.

¹H-NMR (CDCl₃) δ:
0.95 (3H, t, J=7 Hz), 1.33-1.48 (2H, m), 1.57-1.73 (2H, m), 2.17 (3H, s), 2.24 (3H, s), 2.67 (2H, t, J=8 Hz), 2.96 (2H, t, J=7

Hz), 3.97 (2H, s), 4.33 (2H, t, J=7 Hz), 7.47 (1H, t, J=8 Hz), 7.62-7.70 (2H, m), 7.73-7.83 (3H, m), 8.55 (2H, s), 8.70 (1H, s).

Process 2: 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one (yield: 80%) was obtained as a yellow oil according to the same reaction and treatment as the Process 4 of Example 1 by using 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

¹H-NMR (CDCl₃) δ:
0.82-1.00 (3H, m), 1.33-1.47 (2H, m), 1.55-1.73 (2H, m), 2.15 (3H, s), 2.23 (3H, s), 2.55-2.76 (2H, m), 2.95 (2H, t, J=7 Hz), 3.82-4.03 (2H, m), 4.33 (2H, t, J=7 Hz), 7.07-7.33 (1H, m), 7.35-7.57 (3H, m), 7.59-7.80 (1H, m), 7.85-8.15 (1H, m), 8.47-8.62 (1H, m), 8.55 (2H, s).

Example 13

Production of 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one

[Chemical Formula 20]

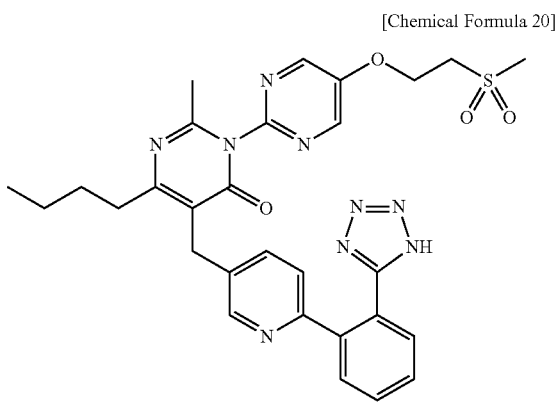 [SMILES: CCCCc1nc(C)n(-c2ncc(OCCS(C)(=O)=O)cn2)c(=O)c1Cc1ccc(-c2ccccc2-c2nnn[nH]2)nc1]

Methanol (0.4 mL) solution of hydrogen peroxide (30% solution, 24 mg, 0.211 mmol) and methanol (0.4 mL) solution of tantalum chloride (1.5 mg, 0.0042 mmol) were added to methanol (1.0) solution of the 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one (24 mg, 0.042 mmol) obtained in the Example 12. The mixture was stirred at room temperature for 12 hours and then the solvent was distilled off. The resulting residues were subjected to silica gel column chromatography (chloroform:methanol:triethylamine=4:1:0.4), to obtain 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one (24 mg, 93%) as a pale yellow amorphous.

¹H-NMR (CDCl₃) δ:
0.94 (3H, t, J=7 Hz), 1.34-1.47 (2H, m), 1.54-1.71 (2H, m), 2.16 (3H, s), 2.66 (2H, t, J=8 Hz), 3.09 (3H, s), 3.55 (2H, t, J=5 Hz), 3.93 (2H, s), 4.64 (2H, t, J=5 Hz), 7.10-7.24 (1H, m), 7.31-7.55 (3H, m), 7.65-7.77 (1H, m), 7.92-8.04 (1H, m), 8.45-8.53 (1H, m), 8.59 (2H, s).

Example 14

Production of 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one

[Chemical Formula 21]

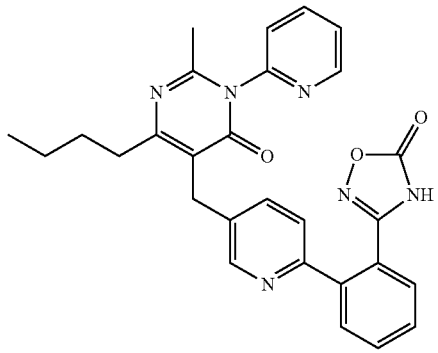

Process 1: 2-{5-{[4-butyl-2-methyl-6-oxo-1-(pyridin-2-yl)-1,6-dihydropyrimidin-5-yl]methyl}pyridin-2-yl}benzonitrile (yield: 61%) was obtained according to the same reaction and treatment as the Process 3 of Example 1 by using 2-aminopyridine instead of the 2-amino-5-methoxypyrimidine in the Process 3 of Example 1.

¹H-NMR (CDCl₃) δ:
0.95 (3H, t, J=7 Hz), 1.43 (2H, sextet, J=8 Hz), 1.61-1.69 (2H, m), 2.17 (3H, s), 2.66-2.70 (2H, m), 3.97 (2H, s), 7.36-7.50 (3H, m), 7.65-7.69 (2H, m), 7.76-7.81 (3H, m), 7.93 (1H, m), 8.67-8.70 (2H, m).

Process 2: Sodium hydrogen carbonate (2.02 mg, 24.0 mmol) was added to a dimethyl sulfoxide (20 mL) solution of hydroxyl amine hydrochloride (1.42 g, 20.4 mmol), and the reaction solution was stirred at 40° C. for 1 hour. The reaction solution was added a dimethyl sulfoxide (3 mL) solution of 2-{5-{[4-butyl-2-methyl-6-oxo-1-(pyridin-2-yl)-1,6-dihydropyrimidin-5-yl]methyl}pyridin-2-yl}benzonitrile (430 mg, 0.987 mmol), and stirred at 90° C. for 19 hours. The reaction solution was added water and extracted with ethyl acetate. The organic layer was combined, washed with water and brine, dried over anhydrous sodium sulfate, and concentrated in vacuo. The residues obtained were subjected to silica gel column chromatography (ethyl acetate), to obtain 2-{5-{[4-butyl-2-methyl-6-oxo-1-(pyridin-2-yl)-1,6-dihydropyrimidin-5-yl]methyl}pyridin-2-yl}-N'-hydroxybenzimidamide (430 mg, 93%) as a white solid.

Process 3: 1,1'-carbonyldiimidazole (490 mg, 3.02 mmol) and 1,8-diazabicyclo[5.4.0]undeca-7-ene (460 mg, 3.02 mmol) were added to a dimethylformamide (25 mL) solution of 2-{5-{[4-butyl-2-methyl-6-oxo-1-(pyridin-2-yl)-1,6-dihydropyrimidin-5-yl]methyl}pyridin-2-yl}-N'-hydroxybenzimidamide (430 mg, 0.918 mmol), and the reaction solution was stirred at room temperature for 3 hours. After completion of the reaction, the reaction solution was added water, and extracted with ethyl acetate. The organic layer was combined, washed with water and brine, dried over anhydrous sodium sulfate, and concentrated in vacuo. The residues obtained were purified by silica gel column chromatography (ethyl acetate), to obtain 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one (160 mg, 35%, 2-step yield) as a pale yellow oil.

¹H-NMR (CDCl₃) δ:
0.94 (3H, t, J=7 Hz), 1.42 (2H, sextet, J=8 Hz), 1.60-1.68 (2H, m), 2.17 (3H, s), 2.64-2.68 (2H, m), 3.93 (2H, s), 7.33-7.56 (6H, m), 7.74-7.77 (2H, m), 7.95 (1H, dd, J=8.2 Hz), 8.45 (1H, s), 8.67 (1H, d, J=4 Hz).

Example 15

Production of 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one

[Chemical Formula 22]

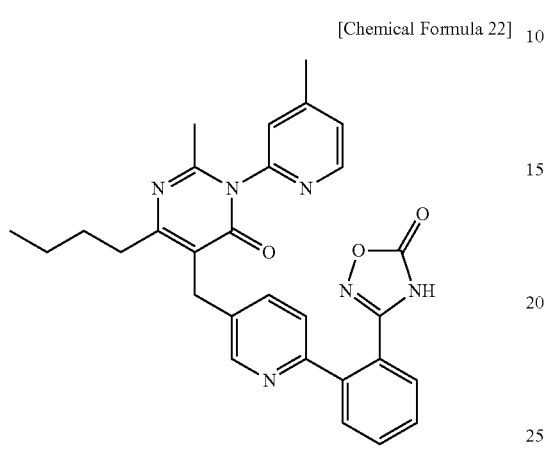

Process 1: 2-{5-{[4-butyl-2-methyl-1-(4-methylpyridin-2-yl)-6-oxo-1,6-dihydropyrimidin-5-yl]methyl}pyridin-2-yl}benzonitrile (yield: 61%) was obtained according to the same reaction and treatment as the Process 3 of Example 1 by using 2-amino-4-methylpyridine instead of the 2-amino-5-methoxypyrimidine in the Process 3 of Example 1.

$^1$H-NMR (CDCl$_3$) δ:

0.95 (3H, t, J=7 Hz), 1.42 (2H, sextet, J=8 Hz), 1.60-1.69 (2H, m), 2.17 (3H, s), 2.45 (3H, s), 2.66-2.70 (2H, m), 3.96 (2H, s), 7.19 (1H, s), 7.24-7.27 (2H, m), 7.48 (1H, m), 7.65-7.69 (2H, m), 7.76-7.82 (2H, m), 8.51 (1H, d, J=5 Hz), 8.70 (1H, s).

Process 2: 2-{5-{[4-butyl-2-methyl-1-(4-methylpyridin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using 2-{5-{[4-butyl-2-methyl-1-(4-methylpyridin-2-yl)-6-oxo-1,6-dihydropyrimidin-5-yl]methyl}pyridin-2-yl}benzonitrile instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 3: 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one (yield: 45%, 2-step yield) was obtained as a pale yellow oil according to the same reaction and treatment as the Process 3 of Example 14 by using 2-{5-{[4-butyl-2-methyl-1-(4-methylpyridin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.95 (3H, t, J=7 Hz), 1.42 (2H, sextet, J=8 Hz), 1.61-1.69 (2H, m), 2.17 (3H, s), 2.46 (3H, s), 2.65-2.69 (2H, m), 3.94 (2H, s), 7.21 (1H, s), 7.24-7.28 (2H, m), 7.37-7.60 (3H, m), 7.78 (1H, dd, J=8.2 Hz), 7.85 (1H, d, J=7 Hz), 8.50-8.51 (2H, m).

Example 16

Production of 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one

[Chemical Formula 23]

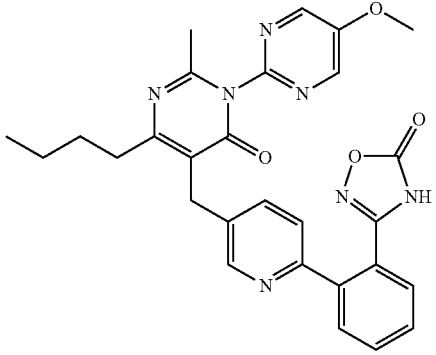

Process 1: 2-{5-{[4-butyl-1-(5-methoxypyrimidin-2-yl)-2-methyl-6-oxo-1,6-dihydropyrimidin-5-yl]methyl}pyridin-2-yl}-N'-hydroxybenzimidamide was obtained according to the same reaction and treatment as the Process 2 of Example 14 by using 2-{5-{[4-butyl-1-(5-methoxypyrimidin-2-yl)-2-methyl-6-oxo-1,6-dihydropyrimidin-5-yl]methyl}pyridin-2-yl}benzonitrile obtained in the Process 3 of Example 1 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one (yield: 48%, 2-step yield) was obtained as a colorless amorphous according to the same reaction and treatment as the Process 3 of Example 14 by using 2-{5-{[4-butyl-1-(5-methoxypyrimidin-2-yl)-2-methyl-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.94 (3H, t, J=7 Hz), 1.43 (2H, quint, J=8 Hz), 1.61-1.68 (2H, m), 2.17 (3H, s), 2.65-2.69 (2H, m), 3.95 (2H, s), 4.01 (3H, s), 7.36-7.69 (4H, m), 7.76-7.86 (2H, m), 8.51 (1H, br), 8.54 (2H, s).

Example 17

Production of 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one

[Chemical Formula 24]

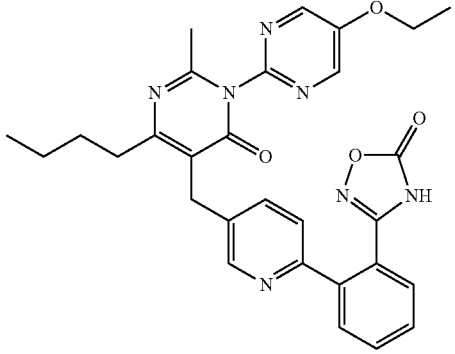

Process 1: 2-{5-{[4-butyl-1-(5-ethoxypyrimidin-2-yl)-2-methyl-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-1-(5-ethoxypyrimidin-2-yl)-2-methyl-6-oxo-1,6-dihydropyrimidin-5-yl]methyl}pyridin-2-yl}benzonitrile obtained in the Process 1 of Example 2 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one (yield: 18%, 2-step yield) was obtained as a pale yellow amorphous according to the same reaction and treatment as the Process 3 of Example 14 by using 2-{5-{[4-butyl-1-(5-ethoxypyrimidin-2-yl)-2-methyl-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.95 (3H, t, J=7 Hz), 1.38-1.48 (2H, m), 1.51 (3H, t, J=7 Hz), 1.62-1.68 (2H, m), 2.17 (3H, s), 2.66-2.70 (2H, m), 3.95 (2H, s), 4.22 (2H, q, J=7 Hz), 7.38-7.61 (4H, m), 7.79 (1H, d, J=7 Hz), 7.90 (1H, d, J=7 Hz), 8.51 (2H, s), 8.54 (1H, s).

Example 18

Production of 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 25]

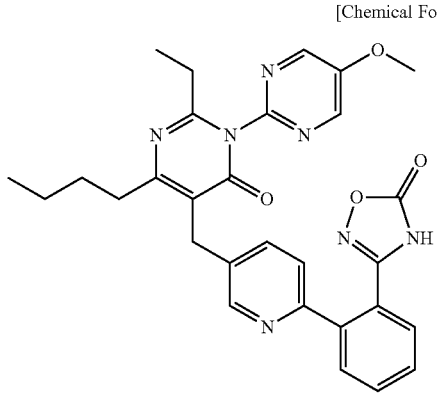

Process 1: 2-{5-{[4-butyl-2-ethyl-1-(5-methoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-ethyl-1-(5-methoxypyrimidin-2-yl)-6-oxo-1,6-dihydropyrimidin-5-yl]methyl}pyridin-2-yl}benzonitrile obtained in the Process 2 of Example 3 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 53%, 2-step yield) was obtained as a white amorphous according to the same reaction and treatment as the Process 3 of Example 14 by using 2-{5-{[4-butyl-2-ethyl-1-(5-methoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.95 (3H, t, J=7 Hz), 1.18 (3H, t, J=7 Hz), 1.36-1.50 (2H, m), 1.61-1.75 (2H, m), 2.32 (2H, q, J=7 Hz), 2.71 (2H, t, J=8 Hz), 3.95 (2H, s), 4.00 (3H, s), 4.79 (1H, br s), 7.38 (1H, d, J=8 Hz), 7.45 (1H, dd, J=8, 1 Hz), 7.51 (1H, dd, J=8, 1 Hz), 7.59 (1H, td, J=8, 2 Hz), 7.79 (1H, dd, J=8, 2 Hz), 7.89 (1H, dd, J=8, 1 Hz), 8.52-8.55 (3H, m).

Example 19

Production of 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one

[Chemical Formula 26]

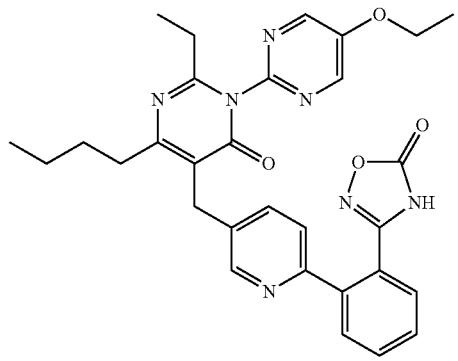

Process 1: 2-{5-{[4-butyl-1-(5-ethoxypyrimidin-2-yl)-2-ethyl-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-1-(5-ethoxypyrimidin-2-yl)-2-ethyl-6-oxo-1,6-dihydropyrimidin-5-yl]methyl}pyridin-2-yl}benzonitrile obtained in the Process 1 of Example 4 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one (yield: 73%, 2-step yield) was obtained as a white amorphous according to the same reaction and treatment as the Process 3 of Example 14 by using 2-{5-{[4-butyl-1-(5-ethoxypyrimidin-2-yl)-2-ethyl-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.94 (3H, t, J=7 Hz), 1.18 (3H, t, J=7 Hz), 1.34-1.47 (2H, m), 1.51 (3H, t, J=7 Hz), 1.60-1.74 (2H, m), 2.32 (2H, q, J=7 Hz), 2.70 (2H, t, J=8 Hz), 3.94 (2H, s), 4.22 (2H, q, J=7 Hz), 7.36 (1H, d, J=8 Hz), 7.41-7.61 (3H, m), 7.77 (1H, dd, J=8, 2 Hz), 7.85 (1H, dd, J=8, 1 Hz), 8.48-8.53 (3H, m).

Example 20

Production of 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 27]

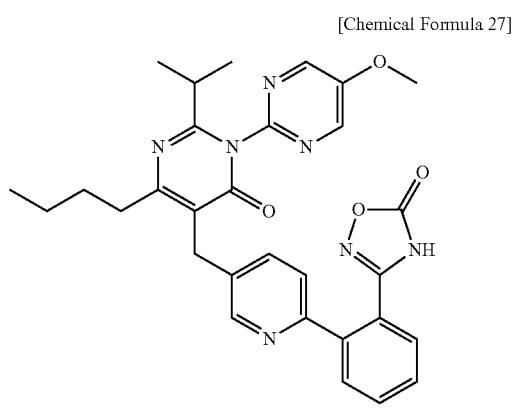 [SMILES: CCCCc1nc(C(C)C)n(-c2ncc(OC)cn2)c(=O)c1Cc1ccc(-c2ccccc2-c2noc(=O)[nH]2)nc1]

Process 1: 2-{5-{[4-butyl-2-isopropyl-1-(5-methoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-isopropyl-1-(5-methoxypyrimidin-2-yl)-6-oxo-1,6-dihydropyrimidin-5-yl]methyl}pyridin-2-yl}benzonitrile obtained in the Process 2 of Example 5 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 60%, 2-step yield) was obtained as a white amorphous according to the same reaction and treatment as the Process 3 of Example 14 by using 2-{5-{[4-butyl-2-isopropyl-1-(5-methoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

¹H-NMR (CDCl₃) δ:
0.95 (3H, t, J=7 Hz), 1.19 (6H, d, J=7 Hz), 1.31-1.49 (2H, m), 1.60-1.75 (2H, m), 2.23-2.35 (1H, m), 2.70 (2H, t, J=8 Hz), 3.93 (2H, s), 4.00 (3H, s), 7.36 (1H, d, J=8 Hz), 7.43 (1H, dd, J=7, 1 Hz), 7.49 (1H, dd, J=7, 1 Hz), 7.57 (1H, td, J=8, 1 Hz), 7.79 (1H, dd, J=8, 2 Hz), 7.85 (1H, dd, J=8, 1 Hz), 8.50 (1H, d, J=2 Hz), 8.53 (2H, s).

Example 21

Production of 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one

[Chemical Formula 28]

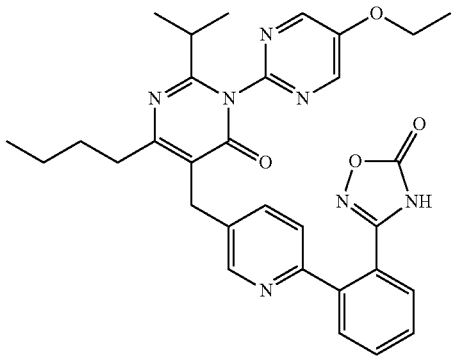

Process 1: 2-{5-{[4-butyl-1-(5-ethoxypyrimidin-2-yl)-2-isopropyl-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-1-(5-ethoxypyrimidin-2-yl)-2-isopropyl-6-oxo-1,6-dihydropyrimidin-5-yl]methyl}pyridin-2-yl}benzonitrile obtained in the Process 1 of Example 6 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one (yield: 66%, 2-step yield) was obtained as a white amorphous according to the same reaction and treatment as the Process 3 of Example 14 by using 2-{5-{[4-butyl-1-(5-ethoxypyrimidin-2-yl)-2-isopropyl-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

¹H-NMR (CDCl₃) δ:
0.95 (3H, t, J=7 Hz), 1.20 (6H, d, J=7 Hz), 1.36-1.46 (2H, m), 1.51 (3H, t, J=7 Hz), 1.62-1.74 (2H, m), 2.23-2.35 (1H, m), 2.72 (2H, t, J=8 Hz), 3.94 (2H, s), 4.22 (2H, q, J=7 Hz), 7.40 (1H, d, J=9 Hz), 7.46 (1H, dd, J=8, 1 Hz), 7.52 (1H, td, J=8, 2 Hz), 7.61 (1H, td, J=8, 2 Hz), 7.82 (1H, dd, J=8, 2 Hz), 7.95 (1H, dd, J=8, 1 Hz), 8.51 (2H, s), 8.58 (1H, d, J=2 Hz).

Example 22

Production of 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 29]

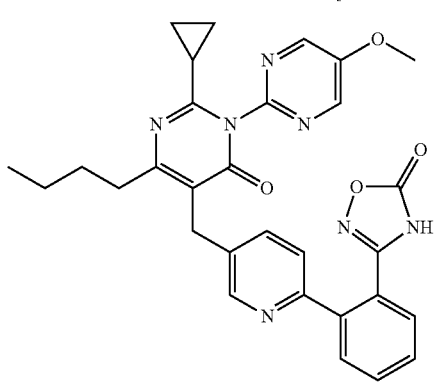

Process 1: 2-{5-{[4-butyl-2-cyclopropyl-1-(5-methoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-cyclopropyl-1-(5-methoxypyrimidin-2-yl)-6-oxo-1,6-dihydropyrimidin-5-yl]methyl}pyridin-2-yl}benzonitrile obtained in the Process 2 of Example 7 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 84%, 2-step yield) was obtained as a white amorphous according to the same reaction and treatment as the Process 3 of Example 14 by using 2-{5-{[4-butyl-2-cyclopropyl-1-(5-methoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.81-0.89 (2H, m), 0.93 (3H, t, J=7 Hz), 1.06-1.15 (1H, m), 1.24 (2H, t, J=4 Hz), 1.32-1.44 (2H, m), 1.55-1.67 (2H, m), 2.63 (2H, t, J=8 Hz), 3.92 (2H, s), 4.00 (3H, s), 7.37 (1H, d, J=8 Hz), 7.45 (1H, d, J=8 Hz), 7.51 (1H, dd, J=8, 1 Hz), 7.59 (1H, td, J=8, 1 Hz), 7.78 (1H, dd, J=8, 2 Hz), 7.89 (1H, d, J=7 Hz), 8.52 (1H, d, J=2 Hz), 8.56 (2H, s).

Example 23

Production of 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 30]

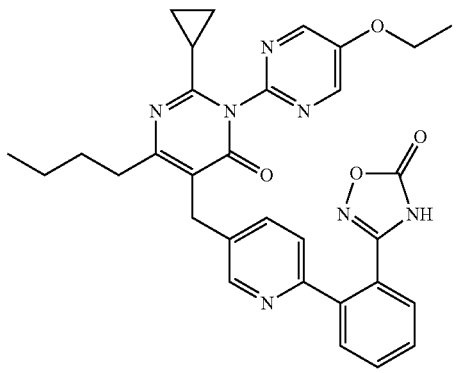

Process 1: 2-{5-{[4-butyl-2-cyclopropyl-1-(5-ethoxypyrimidin-2-yl)-6-oxo-1,6-dihydropyrimidin-5-yl]methyl}pyridin-2-yl}benzonitrile (yield: 65%) was obtained as a yellow oil according to the same reaction and treatment as the Process 3 of Example 1 by using 2-amino-5-ethoxypyrimidine instead of the 2-amino-5-methoxypyrimidine and methyl(Z)-2-{[6-(2-cyanophenyl)pyridin-3-yl]methyl}-3-(cyclopropane carboxamide)-2-heptenoate instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:
0.79-0.87 (2H, m), 0.92 (3H, t, J=8 Hz), 1.09-1.16 (1H, m), 1.18-1.29 (2H, m), 1.30-1.43 (2H, m), 1.51 (3H, t, J=7 Hz), 1.54-1.66 (2H, m), 2.61 (2H, t, J=8 Hz), 3.94 (2H, s), 4.22 (2H, q, J=7 Hz), 7.47 (1H, t, J=8 Hz), 7.57-7.69 (2H, m), 7.71-7.83 (3H, m), 8.54 (2H, s), 8.68 (1H, s).

Process 2: 2-{5-{[4-butyl-2-cyclopropyl-1-(5-ethoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using 2-{5-{[4-butyl-2-cyclopropyl-1-(5-ethoxypyrimidin-2-yl)-6-oxo-1,6-dihydropyrimidin-5-yl]methyl}pyridin-2-yl}benzonitrile instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 3: 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 38%, 2-step yield) was obtained as a colorless crystalline powder according to the same reaction and treatment as the Process 3 of Example 14 by using 2-{5-{[4-butyl-2-cyclopropyl-1-(5-ethoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.76-0.87 (2H, m), 0.92 (3H, t, J=7 Hz), 1.05-1.15 (1H, m), 1.16-1.28 (2H, m), 1.32-1.44 (2H, m), 1.51 (3H, t, J=7 Hz), 1.54-1.66 (2H, m), 2.61 (2H, t, J=8 Hz), 3.91 (2H, s), 4.22 (2H, q, J=7 Hz), 7.34 (1H, d, J=8 Hz), 7.38-7.50 (2H, m), 7.51-7.59 (1H, m), 7.71-7.86 (2H, m), 8.46 (1H, s), 8.54 (2H, s).

Example 24

Production of 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 31]

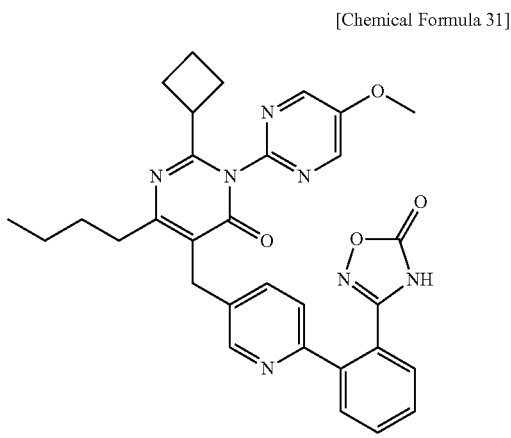 [SMILES: CCCCc1nc(C2CCC2)n(-c2ncc(OC)cn2)c(=O)c1Cc1ccc(-c2ccccc2-c2noc(=O)[nH]2)nc1]

Process 1: 2-{5-{[4-butyl-2-cyclobutyl-1-(5-methoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-cyclobutyl-1-(5-methoxypyrimidin-2-yl)-6-oxo-1,6-dihydropyrimidin-5-yl]methyl}pyridin-2-yl}benzonitrile obtained in the Process 2 of Example 8 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 65%, 2-step yield) was obtained as a white amorphous according to the same reaction and treatment as the Process 3 of Example 14 by using 2-{5-{[4-butyl-2-cyclobutyl-1-(5-methoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.96 (3H, t, J=7 Hz), 1.35-1.51 (2H, m), 1.64-1.85 (6H, m), 2.37-2.53 (2H, m), 2.72 (2H, t, J=8 Hz), 3.04-3.20 (1H, m), 3.94 (2H, s), 4.00 (3H, s), 7.34 (1H, d, J=8 Hz), 7.39-7.44 (1H, m), 7.44-7.49 (1H, m), 7.51-7.59 (1H, m), 7.74-7.83 (2H, m), 8.48 (1H, d, J=2 Hz), 8.52 (2H, s).

Example 25

Production of 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 32]

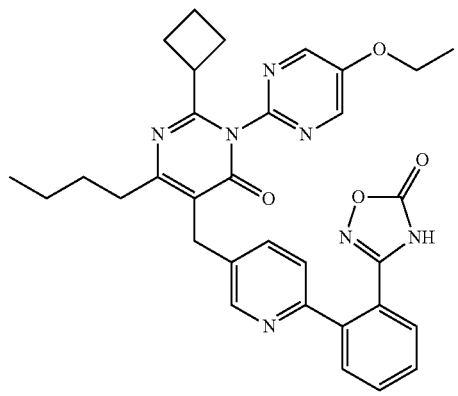

Process 1: 2-{5-{[4-butyl-2-cyclobutyl-1-(5-ethoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-cyclobutyl-1-(5-ethoxypyrimidin-2-yl)-6-oxo-1,6-dihydropyrimidin-5-yl]methyl}pyridin-2-yl}benzonitrile obtained in the Process 1 of Example 9 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 48%, 2-step yield) was obtained as a white amorphous according to the same reaction and treatment as the Process 3 of Example 14 by using 2-{5-{[4-butyl-2-cyclobutyl-1-(5-ethoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.97 (3H, t, J=7 Hz), 1.35-1.47 (2H, m), 1.48-1.83 (9H, m), 2.38-2.52 (2H, m), 2.74 (2H, t, J=8 Hz), 3.03-3.18 (1H, m), 3.95 (2H, s), 4.22 (2H, q, J=7 Hz), 7.40 (1H, d, J=8 Hz), 7.46 (1H, d, J=8 Hz), 7.54 (1H, dd, J=8, 2 Hz), 7.61 (1H, td, J=8, 2 Hz), 7.81 (1H, dd, J=8, 2 Hz), 7.95 (1H, dd, J=8, 1 Hz), 8.49 (2H, s), 8.58 (1H, d, J=2 Hz).

Example 26

Production of 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 33]

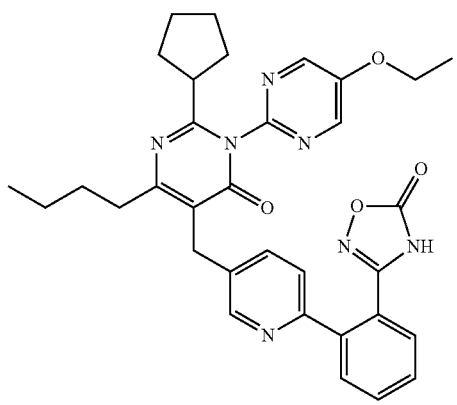

Process 1: 2-{5-{[4-butyl-2-cyclopentyl-1-(5-ethoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-cyclopentyl-1-(5-ethoxypyrimidin-2-yl)-6-oxo-1,6-dihydropyrimidin-5-yl]methyl}pyridin-2-yl}benzonitrile obtained in the Process 2 of Example 10 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 56%, 2-step yield) was obtained as a pale brown amorphous according to the same reaction and treatment as the Process 3 of Example 14 by using 2-{5-{[4-butyl-2-cyclopentyl-1-(5-ethoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.94 (3H, t, J=7 Hz), 1.32-1.57 (7H, m), 1.60-1.85 (6H, m), 1.90-2.06 (2H, m), 2.36-2.52 (1H, m), 2.68 (2H, t, J=7 Hz), 3.93 (2H, s), 4.22 (2H, q, J=7 Hz), 7.35 (1H, d, J=8 Hz), 7.40-7.60 (3H, m), 7.78 (1H, dd, J=8, 2 Hz), 7.83 (1H, dd, J=8, 1 Hz), 8.49 (1H, d, J=2 Hz), 8.51 (2H, s).

Example 27

Production of 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 34]

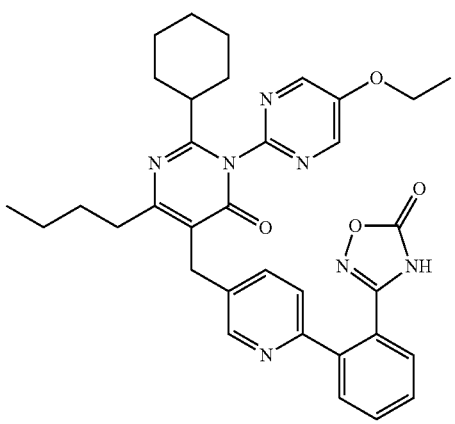

Process 1: 2-{5-{[4-butyl-2-cyclohexyl-1-(5-ethoxypyrimidin-2-yl)-6-oxo-1,6-dihydropyrimidin-5-yl]methyl}pyridin-2-yl}-N'-hydroxybenzimidamide was obtained according to the same reaction and treatment as the Process 2 of Example 14 by using the 2-{5-{[4-butyl-2-cyclohexyl-1-(5-ethoxypyrimidin-2-yl)-6-oxo-1,6-dihydropyrimidin-5-yl]methyl}pyridin-2-yl}benzonitrile obtained in the Process 2 of Example 11 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 60%) was obtained as a pale brown amorphous according to the same reaction and treatment as the Process 3 of Example 14 by using 2-{5-{[4-butyl-2-cyclohexyl-1-(5-ethoxypyrimidin-2-yl)-6-oxo-1,6-dihydropyrimidin-5-yl]methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.89-1.07 (5H, m), 1.34-1.94 (16H, m), 2.68 (2H, t, J=8 Hz), 3.92 (2H, s), 4.23 (2H, q, J=7 Hz), 7.34 (1H, d, J=8 Hz), 7.39-7.49 (2H, m), 7.50-7.59 (1H, m), 7.74-7.83 (2H, m), 8.47 (1H, d, J=2 Hz), 8.51 (2H, s).

Example 28

Production of 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one

[Chemical Formula 35]

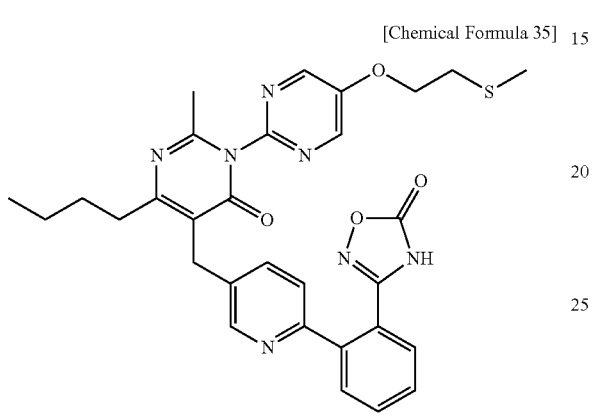

Process 1: 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}-N'-hydroxybenzimidamide was obtained according to the same reaction and treatment as the Process 2 of Example 14 by using the 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}benzonitrile obtained in the Process 1 of Example 12 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

Process 2: 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one (yield: 56%, 2-step yield) was obtained as a pale yellow oil according to the same reaction and treatment as the Process 3 of Example 14 by using 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:
0.95 (3H, t, J=7 Hz), 1.40-1.46 (2H, m), 1.50-1.70 (2H, m), 2.17 (3H, s), 2.24 (3H, s), 2.68-2.71 (2H, m), 2.96 (2H, t, J=7 Hz), 3.96 (2H, s), 4.33 (2H, t, J=7 Hz), 7.40-7.62 (4H, m), 7.66-7.97 (2H, m), 8.55 (2H, s), 8.58 (1H, s)

Example 29

Production of 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one

[Chemical Formula 36]

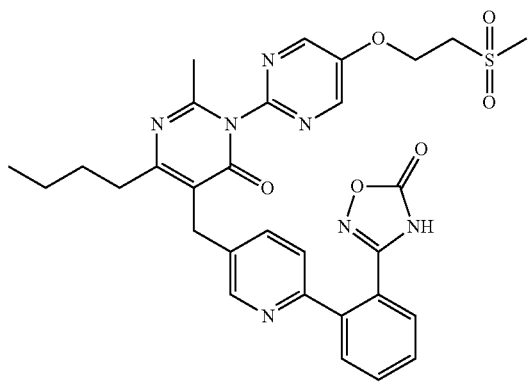

3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one (yield: 63%) was obtained as a colorless oil according to the same reaction and treatment as the Example 13 by using the 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one obtained in the Example 28.

$^1$H-NMR (CDCl$_3$) δ:
0.95 (3H, t, J=7 Hz), 1.40-1.46 (2H, m), 1.65-1.70 (2H, m), 2.18 (3H, s), 2.67-2.71 (2H, m), 3.09 (3H, s), 3.53-3.55 (2H, m), 3.92 (2H, s), 4.63-4.66 (2H, m), 7.36-7.60 (4H, m), 7.74 (1H, d, J=8 Hz), 7.88 (1H, d, J=8 Hz), 8.59 (1H, s), 8.60 (2H, s).

Example 30

Production of 5-{{5-[2-(1H-tetrazol-5-yl)phenyl]pyridin-2-yl}methyl}-6-butyl-2-methyl-3-(pyridin-2-yl)pyrimidin-4(3H)-one

[Chemical Formula 37]

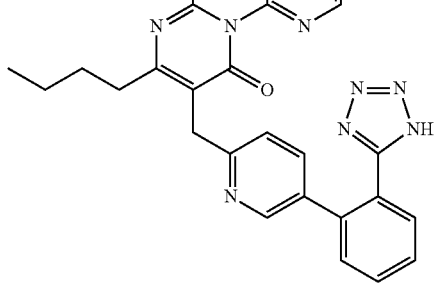

Process 1: methyl 2-{[5-(2-cyanophenyl)pyridin-2-yl]methyl}-3-oxoheptanoate (yield: 69%) was obtained as a yellow oil according to the same reaction and treatment as the Process 1 of Example 1 by using 2-[6-(bromomethyl)pyridin-3-yl]benzonitrile instead of the 2-[5-(bromomethyl)pyridin-2-yl]benzonitrile in the Process 1 of Example 1.

$^1$H-NMR (CDCl$_3$) δ:

0.89 (3H, t, J=7 Hz), 1.24-1.34 (2H, m), 1.54-1.61 (2H, m), 2.59-2.76 (2H, m), 3.37-3.55 (2H, m), 3.73 (3H, s), 4.37 (1H, t, J=7 Hz), 7.33 (1H, d, J=8 Hz), 7.50 (2H, t, J=7 Hz), 7.66-7.70 (1H, m), 7.78-7.83 (2H, m), 8.63 (1H, d, J=2 Hz).

Process 2: Methyl(Z)-3-acetamido-2-{[5-(2-cyanophenyl)pyridin-2-yl]methyl}-2-heptenoate (yield: 100%) was obtained as a yellow oil according to the same reaction and treatment as the Process 2 of Example 1 by using methyl 2-{[5-(2-cyanophenyl)pyridin-2-yl]methyl}-3-oxoheptanoate instead of the methyl 2-{[6-(2-cyanophenyl)pyridin-3-yl]methyl}-3-oxoheptanoate in the Process 2 of Example 1.

$^1$H-NMR (CDCl$_3$) δ:

0.89 (3H, t, J=7 Hz), 1.27-1.40 (2H, m), 1.47-1.59 (2H, m), 2.24 (3H, s), 3.14 (2H, t, J=8 Hz), 3.78 (3H, s), 3.88 (2H, s), 7.42-7.56 (3H, m), 7.65-7.91 (3H, m), 8.63 (1H, s), 10.9 (1H, s).

Process 3:

2-{6-{[4-butyl-2-methyl-6-oxo-1-(pyridin-2-yl)-1,6-dihydropyrimidin-5-yl]methyl}pyridin-3-yl}benzonitrile (yield: 35%) was obtained according to the same reaction and treatment as the Process 3 of Example 1 by using 2-aminopyridine instead of the 2-amino-5-methoxypyrimidine and methyl(Z)-3-acetamido-2-{[5-(2-cyanophenyl)pyridin-2-yl]methyl}-2-heptenoate instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.93 (3H, t, J=7 Hz), 1.42 (2H, sextet, J=8 Hz), 1.60-1.75 (2H, m), 2.17 (3H, s), 2.74-2.78 (2H, m), 4.17 (2H, s), 7.38-7.50 (5H, m), 7.67 (1H, m), 7.77-7.80 (2H, m), 7.93 (1H, m), 8.65 (1H, d, J=2 Hz), 8.68 (1H, d, J=3 Hz).

Process 4:

5-{{5-[2-(1H-tetrazol-5-yl)phenyl]pyridin-2-yl}methyl}-6-butyl-2-methyl-3-(pyridin-2-yl)pyrimidin-4(3H)-one (yield: 79%) was obtained as a pale yellow amorphous according to the same reaction and treatment as the Process 4 of Example 1 by using 2-{6-{[4-butyl-2-methyl-6-oxo-1-(pyrimidin pyridin-2-yl)-1,6-dihydropyrimidin-5-yl]methyl}pyridin-3-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.89 (3H, t, J=7 Hz), 1.30-1.35 (2H, m), 1.50-1.58 (2H, m), 2.18 (3H, s), 2.51-2.54 (2H, m), 3.75 (2H, s), 6.99 (1H, d, J=8 Hz), 7.16 (1H, d, J=8 Hz), 7.31-7.36 (3H, m), 7.48-7.56 (2H, m), 7.83-7.87 (2H, m), 7.97 (1H, s), 8.56 (1H, d, J=4 Hz).

Example 31

Production of 5-{{5-[2-(1H-tetrazol-5-yl)phenyl]pyridin-2-yl}methyl}-6-butyl-3-(5-methoxypyridin-2-yl)-2-methylpyrimidin-4(3H)-one

[Chemical Formula 38]

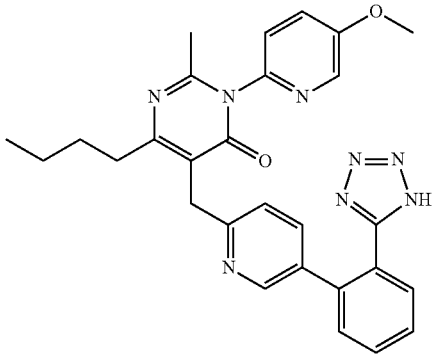

Process 1: 2-{6-{[4-butyl-1-(5-methoxypyridin-2-yl)-2-methyl-6-oxo-1,6-dihydropyrimidin-5-yl]methyl}pyridin-3-yl}benzonitrile (yield: 65%) was obtained as a pale yellow amorphous according to the same reaction and treatment as the Process 3 of Example 1 by using 2-amino-5-methoxypyridine instead of the 2-amino-5-methoxypyrimidine and the methyl(Z)-3-acetamido-2-{[5-(2-cyanophenyl)pyridin-2-yl]methyl}-2-heptenoate obtained in the Process 2 of Example 30 instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.93 (3H, t, J=7 Hz), 1.37-1.46 (2H, m), 1.58-1.66 (2H, m), 2.18 (3H, s), 2.76 (2H, t, J=8 Hz), 3.92 (3H, s), 4.16 (2H, s), 7.27-7.30 (1H, m), 7.38-7.49 (4H, m), 7.65-7.69 (1H, m), 7.77-7.79 (2H, m), 8.30 (1H, d, J=3 Hz), 8.65 (1H, d, J=2 Hz).

Process 2: 5-{{5-[2-(1H-tetrazol-5-yl)phenyl]pyridin-2-yl}methyl}-6-butyl-3-(5-methoxypyridin-2-yl)-2-methylpyrimidin-4(3H)-one (yield: 72%) was obtained as a pale yellow amorphous according to the same reaction and treatment as the Process 4 of Example 1 by using 2-{6-{[4-butyl-1-(5-methoxypyridin-2-yl)-2-methyl-6-oxo-1,6-dihydropyrimidin-5-yl]methyl}pyridin-3-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.87 (3H, t, J=7 Hz), 1.21-1.30 (2H, m), 1.40-1.48 (2H, m), 2.09 (3H, s), 2.38 (2H, t, J=8 Hz), 3.60 (2H, s), 3.90 (3H, s), 7.00 (1H, d, J=8 Hz), 7.14 (2H, dd, J=8, 2 Hz), 7.20 (1H, d, J=9 Hz), 7.34-7.38 (2H, m), 7.53-7.61 (2H, m), 7.84 (1H, d, J=7 Hz), 7.90 (1H, s), 8.21 (1H, d, J=3 Hz).

Example 32

Production of 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one

[Chemical Formula 39]

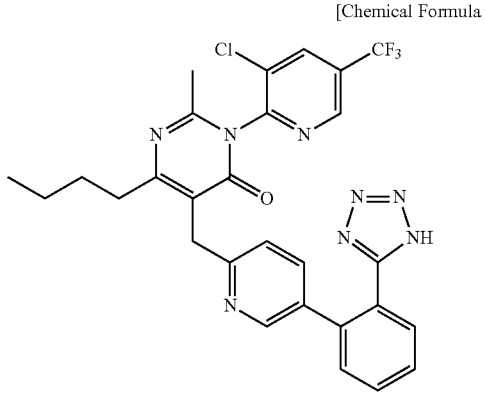

Process 1: 2-{6-{{4-butyl-1-[3-chloro-5-(trifluoromethyl)pyridin-2-yl]-2-methyl-6-oxo-1,6-dihydropyrimidin-5-yl}methyl}pyridin-3-yl}benzonitrile (yield: 41%) was obtained as a pale yellow amorphous according to the same reaction and treatment as the Process 3 of Example 1 by using 2-amino-3-chloro-5-(trifluoromethyl)pyridine instead of the 2-amino-5-methoxypyrimidine and the methyl(Z)-3-acetamido-2-{[5-(2-cyanophenyl)pyridin-2-yl]methyl}-2-heptenoate obtained in the Process 2 of Example 30 instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.94 (3H, t, J=7 Hz), 1.37-1.47 (2H, m), 1.57-1.68 (2H, m), 2.16 (3H, s), 2.70-2.83 (2H, m), 4.19 (2H, s), 7.38 (1H, d, J=8 Hz), 7.46-7.53 (2H, m), 7.65-7.69 (1H, m), 7.77-7.83 (2H, m), 7.89 (1H, m), 8.65 (1H, d, J=2 Hz), 8.84 (1H, s).

Process 2: 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one (yield: 43%) was obtained as a pale yellow amorphous according to the same reaction and treatment as the Process 4 of Example 1 by using 2-{6-{{4-butyl-1-[3-chloro-5-(trifluoromethyl)pyridin-2-yl]-2-methyl-6-oxo-1,6-dihydropyrimidin-5-yl}methyl}pyridin-3-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.87 (3H, t, J=7 Hz), 1.22-1.30 (2H, m), 1.43-1.50 (2H, m), 2.09 (3H, s), 2.35-2.43 (2H, m), 3.55 (2H, dd, J=19, 16 Hz), 6.95 (1H, d, J=8 Hz), 7.11-7.14 (1H, m), 7.38-7.40 (1H, m), 7.54-7.61 (2H, m), 7.86-7.89 (1H, m), 7.94 (1H, m), 8.18 (1H, d, J=2 Hz), 8.81 (1H, s).

Example 33

Production of 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one

[Chemical Formula 40]

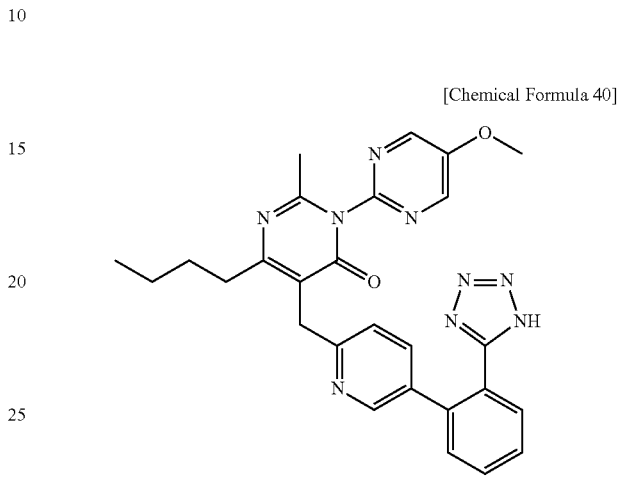

Process 1: 2-{6-{[4-butyl-1-(5-methoxypyrimidin-2-yl)-2-methyl-6-oxo-1,6-dihydropyrimidin-5-yl]methyl}pyridin-3-yl}benzonitrile (yield: 51%) was obtained as a pale yellow amorphous according to the same reaction and treatment as the Process 3 of Example 1 by using the methyl(Z)-3-acetamido-2-{[5-(2-cyanophenyl)pyridin-2-yl]methyl}-2-heptenoate obtained in the Process 2 of Example 30 instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.93 (3H, t, J=7 Hz), 1.36-1.45 (2H, m), 1.57-1.65 (2H, m), 2.16 (3H, s), 2.75 (2H, t, J=8 Hz), 4.00 (3H, s), 4.17 (2H, s), 7.40-7.49 (3H, m), 7.64-7.69 (1H, m), 7.77-7.79 (2H, m), 8.54 (2H, s), 8.65 (1H, d, J=2 Hz).

Process 2: 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one (yield: 52%) was obtained as a pale yellow amorphous according to the same reaction and treatment as the Process 4 of Example 1 by using 2-{6-{[4-butyl-1-(5-methoxypyrimidin-2-yl)-2-methyl-6-oxo-1,6-dihydropyrimidin-5-yl]methyl}pyridin-3-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.86 (3H, t, J=7 Hz), 1.20-1.29 (2H, m), 1.41-1.49 (2H, m), 2.09 (3H, s), 2.43 (2H, t, J=8 Hz), 3.62 (2H, s), 3.98 (3H, s), 7.00 (1H, d, J=8 Hz), 7.13 (1H, dd, J=8, 2 Hz), 7.39 (1H, d, J=8 Hz), 7.51-7.60 (2H, m), 7.84 (1H, d, J=8 Hz), 7.95 (1H, d, J=2 Hz), 8.48 (2H, s).

Example 34

Production of 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one

[Chemical Formula 41]

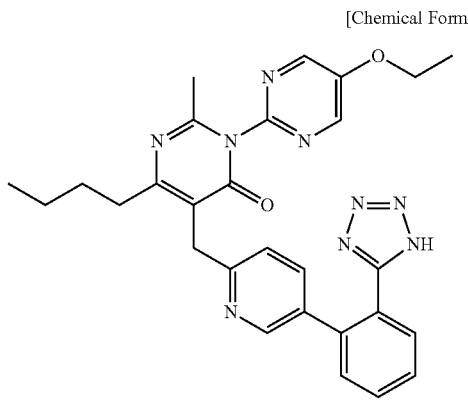

Process 1: 2-{6-{[4-butyl-1-(5-ethoxypyrimidin-2-yl)-2-methyl-6-oxo-1,6-dihydropyrimidin-5-yl]methyl}pyridin-3-yl}benzonitrile (yield: 70%) was obtained as a pale yellow amorphous according to the same reaction and treatment as the Process 3 of Example 1 by using 2-amino-5-ethoxypyrimidine instead of the 2-amino-5-methoxypyrimidine and the methyl(Z)-3-acetamido-2-{[5-(2-cyanophenyl)pyridin-2-yl]methyl}-2-heptenoate obtained in the Process 2 of Example 30 instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.92 (3H, t, J=7 Hz), 1.36-1.45 (2H, m), 1.51 (3H, t, J=7 Hz), 1.57-1.65 (2H, m), 2.16 (3H, s), 2.75 (2H, t, J=8 Hz), 4.18 (2H, s), 4.22 (2H, q, J=7 Hz), 7.41-7.52 (3H, m), 7.64-7.68 (1H, m), 7.77-7.81 (2H, m), 8.52 (2H, s), 8.63-8.65 (1H, m).

Process 2: 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one (yield: 63%) was obtained as a yellow amorphous according to the same reaction and treatment as the Process 4 of Example 1 by using 2-{6-{[4-butyl-1-(5-ethoxypyrimidin-2-yl)-2-methyl-6-oxo-1,6-dihydropyrimidin-5-yl]methyl}pyridin-3-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ:

0.86 (3H, t, J=7 Hz), 1.18-1.29 (2H, m), 1.40-1.50 (2H, m), 1.49 (3H, t, J=7 Hz), 2.09 (3H, s), 2.42 (2H, t, J=8 Hz), 3.61 (2H, s), 4.20 (q, 2H, J=7 Hz), 7.00 (1H, d, J=8 Hz), 7.12 (1H, dd, J=8, 2 Hz), 7.39 (1H, d, J=8 Hz), 7.51-7.61 (2H, m), 7.86 (1H, d, J=7 Hz), 7.74 (1H, d, J=2 Hz), 8.46 (2H, s).

Example 35

Production of 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one

[Chemical Formula 42]

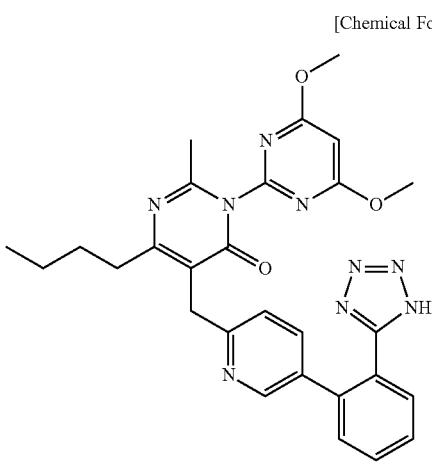

Process 1: 2-{6-{[4-butyl-1-(4,6-dimethoxypyrimidin-2-yl)-2-methyl-6-oxo-1,6-dihydropyrimidin-5-yl]methyl}pyridin-3-yl}benzonitrile (yield: 49%) was obtained as a pale yellow amorphous according to the same reaction and treatment as the Process 3 of Example 1 by using 2-amino-4,6-dimethoxypyrimidine instead of the 2-amino-5-methoxypyrimidine and the methyl(Z)-3-acetamido-2-{[5-(2-cyanophenyl)pyridin-2-yl]methyl}-2-heptenoate obtained in the Process 2 of Example 30 instead of the methyl(Z)-3-acetamido-2-{[6-(2-cyanophenyl)pyridin-3-yl]methyl}-2-heptenoate in the Process 3 of Example 1.

$^1$H-NMR (CDCl$_3$) δ:

0.93 (3H, t, J=7 Hz), 1.38-1.47 (2H, m), 1.56-1.67 (2H, m), 2.24 (3H, s), 2.76 (2H, t, J=8 Hz), 3.96 (6H, s), 4.19 (2H, s), 6.12 (1H, s), 7.45-7.50 (3H, m), 7.65-7.69 (1H, m), 7.77-7.82 (2H, m), 8.66 (1H, d, J=2 Hz).

Process 2: 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one (yield: 53%) was obtained as a pale yellow amorphous according to the same reaction and treatment as the Process 4 of Example 1 by using 2-{6-{[4-butyl-1-(4,6-dimethoxypyrimidin-2-yl)-2-methyl-6-oxo-1,6-dihydropyrimidin-5-yl]methyl}pyridin-3-yl}benzonitrile instead of the 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of Example 1.

$^1$H-NMR (CDCl$_3$) δ: 0.88 (3H, t, J=7 Hz), 1.22-1.32 (2H, m), 1.43-1.50 (2H, m), 2.17 (3H, s), 2.42 (2H, t, J=8 Hz), 3.62 (2H, s), 3.89 (6H, s), 6.06 (1H, s), 7.02 (1H, d, J=8 Hz), 7.14 (1H, dd, J=8, 2 Hz), 7.40 (1H, d, J=8 Hz), 7.53-7.62 (2H, m), 7.31 (1H, d, J=8 Hz), 7.95 (1H, s).

Example 36

Production of 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one

[Chemical Formula 43]

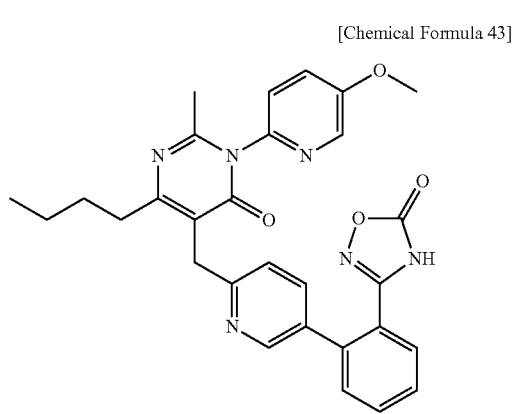 [SMILES: CCCCc1nc(C)n(-c2ccc(OC)cn2)c(=O)c1Cc1ccc(-c2ccccc2-c2noc(=O)[nH]2)cn1]

Process 1: 2-{6-{[4-butyl-1-(5-methoxypyridin-2-yl)-2-methyl-6-oxo-1,6-dihydropyrimidin-5-yl]methyl}pyridin-3-yl}-N'-hydroxybenzimidamide (yield: 64%) was obtained as a pale yellow amorphous according to the same reaction and treatment as the Process 2 of Example 14 by using the 2-{6-{[4-butyl-1-(5-methoxypyridin-2-yl)-2-methyl-6-oxo-1,6-dihydropyrimidin-5-yl]methyl}pyridin-3-yl}benzonitrile obtained in the Process 1 of Example 31 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

$^1$H-NMR (CDCl$_3$) δ:

0.90 (3H, t, J=7 Hz), 1.34-1.43 (2H, m), 1.54-1.62 (2H, m), 2.16 (3H, s), 2.71 (2H, t, J=8 Hz), 3.91 (3H, s), 4.13 (2H, s), 4.50 (2H, s), 7.29-7.42 (5H, m), 7.45-7.49 (1H, m), 7.55-7.57 (1H, m), 7.66-7.69 (1H, m), 8.29 (1H, d, J=3 Hz), 8.60 (1H, d, J=2 Hz).

Process 2: 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one (yield: 70%) was obtained as a pale yellow amorphous according to the same reaction and treatment as the Process 3 of Example 14 by using 2-{6-{[4-butyl-1-(5-methoxypyridin-2-yl)-2-methyl-6-oxo-1,6-dihydropyrimidin-5-yl]methyl}pyridin-3-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.92 (3H, t, J=7 Hz), 1.30-1.39 (2H, m), 1.49-1.57 (2H, m), 2.11 (3H, s), 2.51 (2H, t, J=8 Hz), 3.62 (2H, s), 3.91 (3H, s), 7.15 (1H, d, J=8 Hz), 7.23 (2H, d, J=9 Hz), 7.32-7.39 (2H, m), 7.48-7.52 (2H, m), 7.57-7.61 (1H, m), 7.70 (1H, d, J=8 Hz), 7.99 (1H, s), 8.18 (1H, d, J=3 Hz).

Example 37

Production of 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one

[Chemical Formula 44]

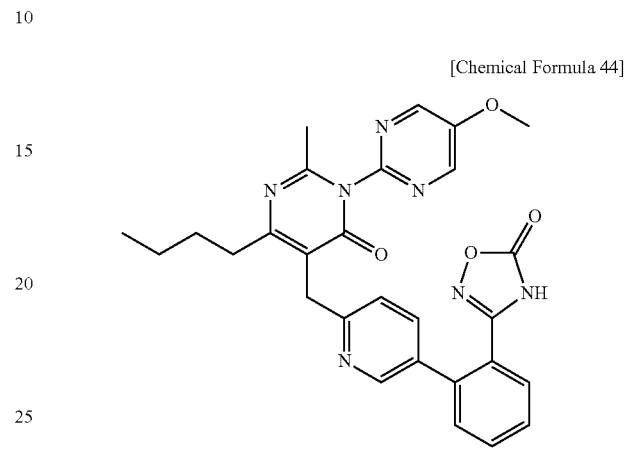

Process 1: 2-{6-{[4-butyl-1-(5-methoxypyrimidin-2-yl)-2-methyl-6-oxo-1,6-dihydropyrimidin-5-yl]methyl}pyridin-3-yl}-N'-hydroxybenzimidamide (yield: 50%) was obtained as a pale yellow amorphous according to the same reaction and treatment as the Process 2 of Example 14 by using the 2-{6-{[4-butyl-1-(5-methoxypyrimidin-2-yl)-2-methyl-6-oxo-1,6-dihydropyrimidin-5-yl]methyl}pyridin-3-yl}benzonitrile obtained in the Process 1 of Example 33 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

$^1$H-NMR (CDCl$_3$) δ:

0.90 (3H, t, J=7 Hz), 1.34-1.43 (2H, m), 1.54-1.62 (2H, m), 2.15 (3H, s), 2.73 (2H, t, J=8 Hz), 3.99 (3H, s), 4.13 (2H, s), 4.50 (2H, s), 7.28-7.42 (3H, m), 7.45-7.49 (1H, m), 7.53-7.57 (1H, m), 7.66-7.69 (1H, m), 8.53 (2H, s), 8.59 (1H, d, J=2 Hz).

Process 2: 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one (yield: 85%) was obtained as a pale yellow amorphous according to the same reaction and treatment as the Process 3 of Example 14 by using 2-{6-{[4-butyl-1-(5-methoxypyrimidin-2-yl)-2-methyl-6-oxo-1,6-dihydropyrimidin-5-yl]methyl}pyridin-3-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.90 (3H, t, J=7 Hz), 1.27-1.36 (2H, m), 1.45-1.53 (2H, m), 2.11 (3H, s), 2.45 (2H, t, J=8 Hz), 3.56 (2H, s), 4.00 (3H, s), 7.12 (1H, d, J=8 Hz), 7.38 (1H, d, J=8 Hz), 7.50-7.60 (2H, m), 7.60-7.64 (1H, m), 7.72 (1H, d, J=1 Hz), 7.90 (1H, s), 8.51 (2H, s).

Example 38

Production of 3-{2-{6-{[4-butyl-1-(5-ethoxypyrimi-din-2-yl)-2-methyl-6-oxo-1,6-dihydropyrimidin-5-yl]methyl}pyridin-3-yl}phenyl}-1,2,4-oxadiazol-5(4H)-one

[Chemical Formula 45]

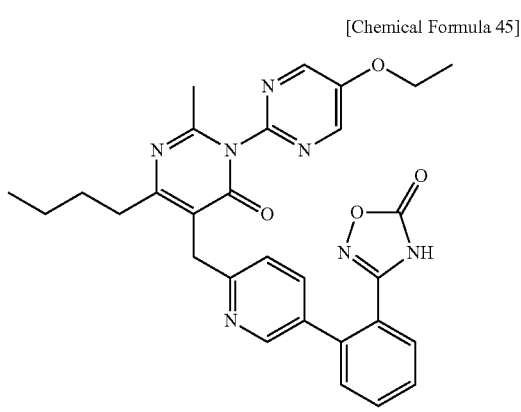 [SMILES: CCCCc1nc(C)n(-c2ncc(OCC)cn2)c(=O)c1Cc1ccc(-c2ccccc2-c2noc(=O)[nH]2)cn1]

Process 1: 2-{6-{[4-butyl-1-(5-ethoxypyrimidin-2-yl)-2-methyl-6-oxo-1,6-dihydropyrimidin-5-yl]methyl}pyridin-3-yl}-N'-hydroxybenzimidamide (yield: 52%) was obtained as a pale yellow amorphous according to the same reaction and treatment as the Process 2 of Example 14 by using the 2-{6-{[4-butyl-1-(5-ethoxypyrimidin-2-yl)-2-methyl-6-oxo-1,6-dihydropyrimidin-5-yl]methyl}pyridin-3-yl}benzonitrile obtained in the Process 1 of Example 34 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

$^1$H-NMR (CDCl$_3$) δ:

0.90 (3H, t, J=7 Hz), 1.35-1.43 (2H, m), 1.50 (3H, t, J=7 Hz), 1.51-1.62 (2H, m), 2.15 (3H, s), 2.72 (2H, t, J=8 Hz), 4.13 (2H, s), 4.21 (2H, q, J=7 Hz), 4.51 (2H, s), 7.28-7.49 (4H, m), 7.55-7.57 (1H, m), 7.66-7.69 (1H, m), 8.50 (2H, s), 8.59-8.60 (1H, m).

Process 2: 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5(4H)-one (yield: 89%) was obtained as a pale yellow amorphous according to the same reaction and treatment as the Process 3 of Example 14 by using 2-{6-{[4-butyl-1-(5-ethoxypyrimidin-2-yl)-2-methyl-6-oxo-1,6-dihydropyrimidin-5-yl]methyl}pyridin-3-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_3$) δ:

0.90 (3H, t, J=7 Hz), 1.27-1.36 (2H, m), 1.45-1.52 (5H, m), 2.11 (3H, s), 2.49 (2H, t, J=8 Hz), 3.59 (2H, s), 4.22 (2H, q, J=7 Hz), 7.18 (1H, d, J=8 Hz), 7.38 (1H, d, J=8 Hz), 7.50-7.55 (2H, m), 7.60-7.64 (1H, m), 7.72 (1H, d, J=8 Hz), 7.93-7.97 (1H, m), 8.49 (2H, s).

Example 39

Production of 3-{2-{6-{[4-butyl-1-(4,6-dimethoxy-pyrimidin-2-yl)-2-methyl-6-oxo-1,6-dihydropyrimidin-5-yl]methyl}pyridin-3-yl}phenyl}-1,2,4-oxadiazol-5(4H)-one

[Chemical Formula 46]

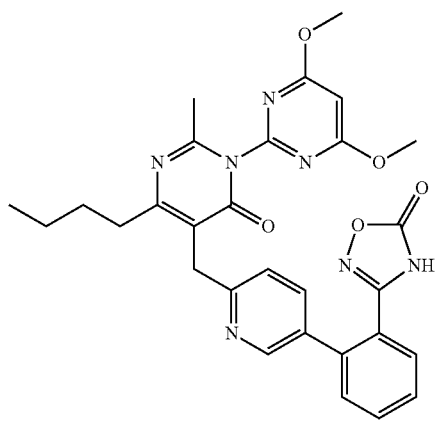

Process 1:

2-{6-{[4-butyl-1-(4,6-dimethoxypyrimidine-2-yl)-2-methyl-6-oxo-1,6-dihydropyrimidin-5-yl]methyl}pyridin-3-yl}-N'-hydroxybenzimidamide (yield: 47%) was obtained as a pale yellow amorphous according to the same reaction and treatment as the Process 2 of Example 14 by using the 2-{6-{[4-butyl-1-(4,6-dimethoxypyrimidin-2-yl)-2-methyl-6-oxo-1,6-dihydropyrimidin-5-yl]methyl}pyridin-3-yl}benzonitrile obtained in the Process 1 of Example 35 instead of the 2-{5-{[4-butyl-2-methyl-6-oxo-1-(pyridin-2-yl)-1,6-dihydropyrimidin-5-yl]methyl}pyridin-2-yl}benzonitrile in the Process 2 of Example 14.

$^1$H-NMR (CDCl$_3$) δ:

0.92 (3H, t, J=7 Hz), 1.36-1.45 (2H, m), 1.56-1.64 (2H, m), 2.23 (3H, s), 2.73 (2H, t, J=8 Hz), 3.95 (6H, s), 4.14 (2H, s), 4.49 (2H, s), 6.12 (1H, s), 7.32-7.43 (3H, m), 7.46-7.50 (1H, m), 7.56-7.58 (1H, m), 7.69-7.71 (1H, m), 8.57-8.61 (1H, m).

Process 2: 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one (yield: 52%) was obtained as a pale yellow amorphous according to the same reaction and treatment as the Process 3 of Example 14 by using 2-{6-{[4-butyl-1-(4,6-dimethoxypyrimidin-2-yl)-2-methyl-6-oxo-1,6-dihydropyrimidin-5-yl]methyl}pyridin-3-yl}-N'-hydroxybenzimidamide instead of the 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of Example 14.

$^1$H-NMR (CDCl$_2$) δ:

0.92 (3H, t, J=7 Hz), 1.31-1.40 (2H, m), 1.50-1.58 (2H, m), 2.18 (3H, s), 2.51 (2H, t, J=8 Hz), 3.67 (2H, s), 3.92 (6H, s), 6.08 (1H, s), 7.21 (1H, d, J=8 Hz), 7.41 (1H, d, J=8 Hz), 7.50-7.56 (2H, m), 7.63 (1H, t, J=8 Hz), 7.74 (1H, d, J=8 Hz), 8.01 (1H, d, J=2 Hz).

Test Example 1

Angiotensin II Receptor Antagonistic Activity in Isolated Rabbit Blood Vessels

By using a specimen of isolated rabbit blood vessels, antagonistic activity of the compounds of the invention against angiotensin II type 1 receptor was estimated from a dose-response curve of angiotensin II-induced blood vessel contraction. Specifically, the specimen of thoracic aorta ring of a rabbit (New Zealand White: male, 2.4 to 3.0 kg) was suspended in a magnus bath filled with Krebs-Henseleite buffer (composition: 118 mM NaCl, 4.7 mM KCl, 2.55 mM $CaCl_2$, 1.18 mM $MgSO_4$, 1.18 mM $KH_2PO_4$, 24.88 mM $NaHCO_3$, and 11.1 mM D-glucose), and angiotensin II (10 nM)-induced contraction was obtained in the presence of the compounds of each test (1 nmol/L to 10 μmol/L). During the measurement, the inside temperature of the magnus bath was maintained at 37° C. and the bath was continuously ventilated with a sufficient amount of mixed gas (95% $O_2$ and 5% $CO_2$). The angiotensin II-induced contraction was converted into a relative value (%) that is based on the angiotensin II (0.1 μM)-induced contraction in the absence of the compounds of each example.

As a result, it was found that the compound described in each example has an angiotensin II inhibition activity at 0.1 μM concentration. The inhibition activities (%) of angiotensin II (10 nM) at a concentration of 0.1 μM of the test compounds are shown in Table 1. As shown in Table 1, it was confirmed that the compound of the present invention has potent angiotensin II receptor antagonistic activity, which is equivalent to that of telmisartan. Under the same condition, the angiotensin II activity inhibition rate of telmisartan was 85.3%.

TABLE 1

| Example No. | Angiotensin II activity inhibitiom rate (%) at 0.1 μM concentration |
|---|---|
| 1 | 100 |
| 2 | 90.8 |
| 12 | 100 |
| 13 | 100 |
| 14 | 59.3 |
| 15 | 78.3 |
| 16 | 72.9 |
| 17 | 52.1 |
| 21 | 70.3 |
| 22 | 59.5 |
| 23 | 75.2 |
| 28 | 86.5 |
| 29 | 96.3 |

Test Example 2

PPARγ Activation Activity

The agonistic activity of the compounds of the invention on PPARγ was measured based on the transfection assay using COS7 cells (DS Pharma Biomedical Co., Ltd., Osaka, Japan), which are the cell line derived from the kidney of the African green monkey. COS7 cells were cultured under 5% $CO_2$ concentration, and DMEM medium containing 10% fetal bovine serum, glutamic acid, and antibiotics was used as a medium.

As an expression vector, a chimera in which DNA binding domain of Gal4, which is a yeast transcription factor, and ligand binding domain of human PPARγ2 are fused, i.e., a fused product between the amino acids 1 to 147 of Gal4 transcription factor and the amino acids 182 to 505 of human PPARγ2, was used. Furthermore, as a reporter vector, a firefly luciferase containing five copies of Gal4 recognition sequence in the promoter region was used. Plasmid transfection to the cells was performed according to a method which uses jetPEI (trade name, manufactured by Funakoshi Co., Ltd., Tokyo, Japan). Furthermore, β-galactosidase expression vector was employed as an internal standard.

After the transfection of the cells, the medium was replaced with a DMEM medium (containing 1% serum) added with the test compound, and the cells were further cultured for 16 hours. After that, the luciferase activity and β-galactosidase activity in the cell lysis solution were measured.

For the present test, dimethyl sulfoxide (DMSO) was used for dissolution and dilution of the test compounds, and during the cell treatment, the DMSO concentration in DMEM medium (containing 1% serum) was adjusted to 0.1%. As a positive compound, rosiglitazone (trade name, manufactured by ALEXIS Corporation, Switzerland) was used. The luciferase activity (%) of the test compounds (1 to 30 μmol/L) was calculated when the luciferase activity of rosiglitazone (3 to 10 μmol/L) is 100% and the luciferase activity in the absence of the test compound is 0%. The 50% effective concentration of the test compound ($EC_{50}$, 50% effect concentration) was calculated by using SAS Preclinical Package Ver 5.0 (trade name, manufactured by SAS institute Japan Co., Tokyo, Japan), which is a statistical analysis program.

As a result, it was found that the each compound described in Examples has a PPARγ activation activity at 30 μM concentration. $EC_{50}$ values of these compounds are described in Table 2. As shown in Table 2, it was confirmed that the compounds of the present invention have a potent PPARγ activation activity. Under the same condition, the PPARγ activation activity of telmisartan, i.e., $EC_{50}$, was 1 to 5 μM.

TABLE 2

| Example No. | $EC_{50}$ (μM) |
|---|---|
| 6 | 1.36 |
| 15 | 3.61 |
| 17 | 3.12 |
| 18 | 3.39 |
| 19 | 1.50 |
| 20 | 0.85 |
| 21 | 0.45 |
| 22 | 1.55 |
| 23 | 0.76 |
| 24 | 1.46 |
| 25 | 0.82 |
| 26 | 0.38 |
| 27 | 0.67 |
| 32 | 2.74 |

From the results obtained above, it was confirmed that the compounds represented by the general formula (I) of the present invention have both a potent angiotensin II receptor antagonistic activity and a PPARγ activation activity. Thus, it was found that the compounds represented by the formula (I) of the present invention and pharmaceutically acceptable salts thereof are useful as an effective component of a prophylactic and/or therapeutic agent for disorders involved with angiotensin II and PPARγ, for example, hypertension, heart diseases, angina pectoris, cerebrovascular disorders, cerebral circulatory disorders, ischemic peripheral circulatory disorders, renal diseases, arteriosclerosis, inflammatory diseases, type 2 diabetes, diabetic complications, insulin resistance syndrome, syndrome X, metabolic syndrome, and hyperinsulinemia.

Test Example 3

Investigation of Hypotensive Activity with Tail Cuff Method

By using 19-week old spontaneously hypertensive rats (SHR), the body weight and the systolic blood pressure (SBP)

of each rat were measured before administration of the medicine, and group separation was performed by blocking assignment so that there was no variation of these values between respective groups. Solvent control (0.5% methyl cellulose solution, MC), 3 mg/kg telmisartan, 3 and 10 mg/kg of the compound of Example 21, and 3 and 10 mg/kg of the compound of Example 23 were orally administered iteratively for 7 days, once a day. The blood pressure and the heart beat rate were measured with tail cuff method at 4, 24, and 72 hours after the administration of the final administration day. Specifically, the rat was put into a cylindrical positioner, maintained at 37° C., and the blood pressure and the heart beat rate were measured from the tail of the rat during the resting state using a non-invasive blood pressure meter (trade name: BP-98A, manufactured by Softron Co., Ltd., Tokyo, Japan). The blood pressure and the heart beat rate were measured for each individual three times or more in a row. When the difference of the systolic blood pressures between the consecutive measurement values was 5 mmHg or less, the average values of these measurement values were taken as data, except for the first measurement.

The results are shown in FIG. 1. The vertical axis of FIG. 1 represents the change of the values from pre-administration in systolic blood pressure, and Vehicle, Telmisartan, Compound 23, and Compound 21 represent solvent control, telmisartan, the compound of Example 23, and the compound of Example 21, respectively. The data in FIG. 1 represents average values of each individual ±standard error, and the black color represents results after 4 hours, the ash color represents results after 24 hours, and the white color represents results after 72 hours. As the results, it was confirmed that the compound of Example 21 and the compound of Example 23 had potent blood pressure lowering activity dose-dependently that was equivalent or more to telmisartan, and maintained the activity for a long time.

Test Example 4

Investigation of Impaired Glucose Tolerance Improving Activity in Type 2 Diabetes Model Mouse By using 7-week old db/db mice, the body weight and the plasma glucose concentration of each mouse were measured before administration of the medicine, and group separation was performed by blocking assignment so that there was no variation of these values between respective groups. Solvent control (0.5% MC), 5 mg/kg rosiglitazone, 30 mg/kg telmisartan, 10 mg/kg of the compound of Example 23, and 30 mg/kg of the compound of Example 21 were orally administered iteratively for 4 weeks, once a day. Blood collecting was performed from the orbital vein plexus, and the plasma glucose concentration was measured at 2 weeks after the initiation of the administration. Furthermore, oral glucose tolerance test was performed at 4 weeks after the initiation of the administration. Specifically, the mouse was fasted for 24 hours from the night before the glucose tolerance test, and then a glucose solution was orally administered at a dose of 2 g/kg. The blood was collected from the tail vein of the mouse at 15, 30, 60, and 120 minutes after the administration of the glucose solution, and the concentration of the plasma glucose was measured. The area surrounded with the measured plasma glucose concentration and the time was taken as the area under the curve (AUC), and AUC for 120 minutes after administration of the glucose solution was estimated from the trapezoidal method.

Figure 2:
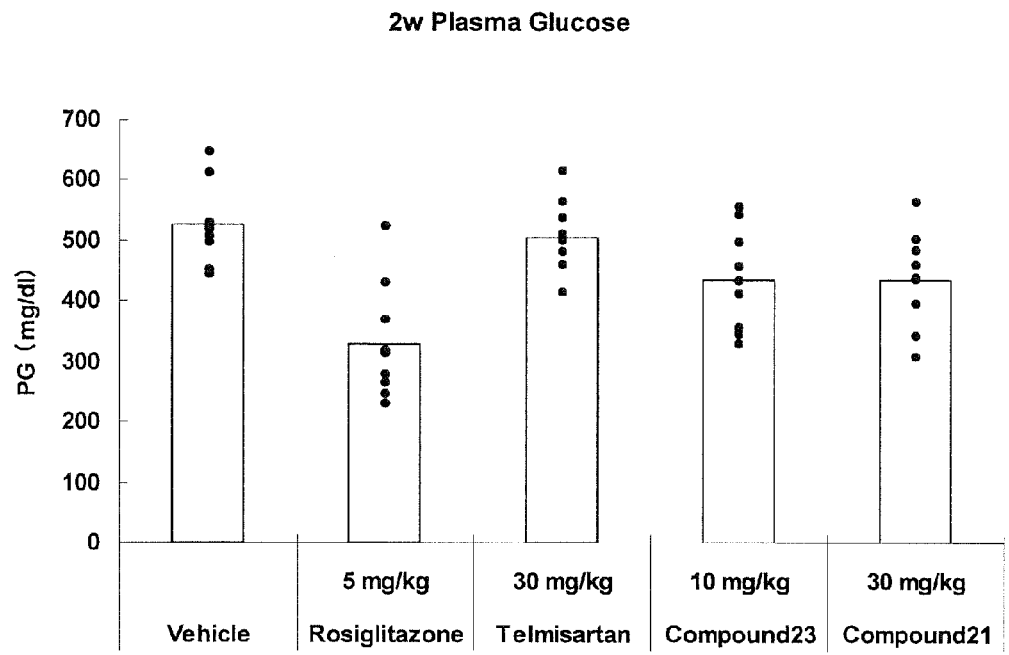
FIG. 2 illustrates results of investigations for impaired glucose tolerance-improving activity in type 2 diabetes model mouse. The vertical axis of FIG. 2 represents plasma glucose concentration, and Vehicle, Rosiglitazone, Telmisartan, Compound 23, and Compound 21 of the horizontal axis represent solvent control, rosiglitazone, telmisartan, the compound of Example 23, and the compound of Example 21, respectively. The data in FIG. 2 represents individual values and average values of each individual.
Figure 3:
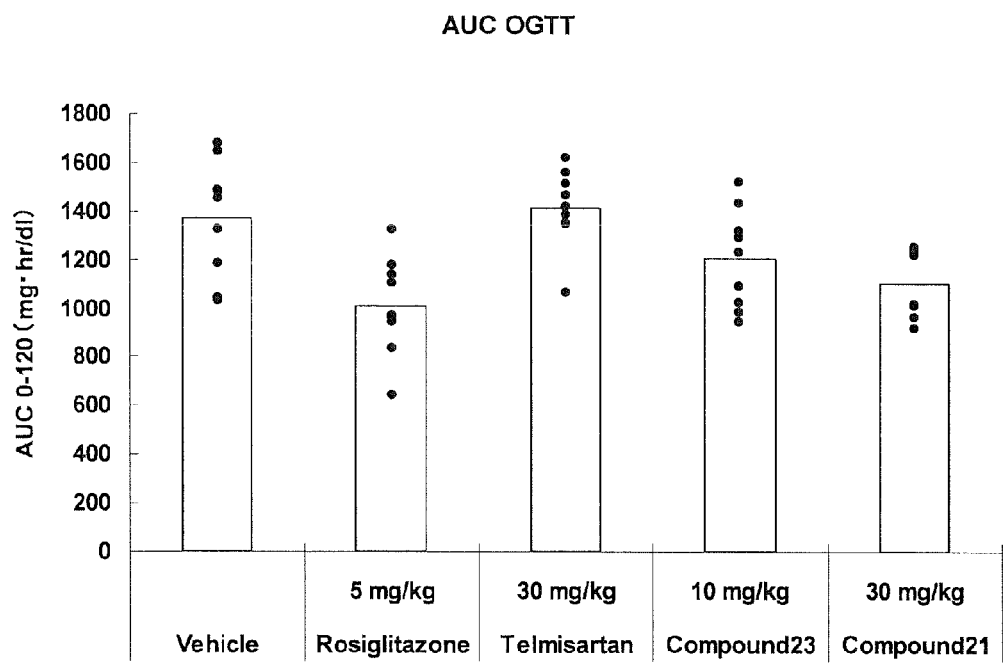
FIG. 3 illustrates results of investigations for impaired glucose tolerance-improving activity in type 2 diabetes model mouse. The vertical axis of FIG. 3 represents the area under the curve surrounded with plasma glucose concentration and time (for 120 minutes after administration of glucose solution), and Vehicle, Rosiglitazone, Telmisartan, Compound 23, and Compound 21 of the horizontal axis represent solvent control, rosiglitazone, telmisartan, the compound of Example 23, and the compound of Example 21, respectively. The data in FIG. 3 represents individual values and average values of each individual.

The results are shown in FIGS. 2 and 3. Vehicle, Rosiglitazone, Telmisartan, Compound 23, and Compound 21 in FIGS. 2 and 3 represent solvent control, rosiglitazone, telmisartan, the compound of Example 23, and the compound of Example 21, respectively. The vertical axis of FIG. 2 represents the plasma glucose concentration. The data in FIG. 2 represents individual values and average values of each individual. The vertical axis of FIG. 3 represents the area under the curve surrounded with the plasma glucose concentration and the time (for 120 minutes after administration of the glucose solution). The data in FIG. 3 represents individual values and average values of each individual. As the results, it was confirmed that both of the compound of Example 21 and the compound of Example 23 had remarkable lowering activity of the plasma glucose concentration (FIG. 2). Furthermore, it was found that both of the compound of Example 21 and the compound of Example 23 had activities of remarkably lowering AUC in the glucose tolerance test (FIG. 3), and had activities of improving abnormal glucose metabolism and impaired glucose tolerance. Such activities were not confirmed for the telmisartan administration group.

Test Example 5

Investigation of Activity for Diabetic Nephropathy

By using 8-week old Zucker diabetic fatty (ZDF) rats, the body weight, the elimination amount of urinary total protein (UTP), the plasma triglyceride concentration (TG), and the plasma total cholesterol concentration (TC) of each rat were measured before administration of the medicine, and group separation was performed by blocking assignment so that there was no variation of these values between respective groups. Solvent control (0.5% MC), 3 mg/kg telmisartan, 3 mg/kg of the compound of Example 21, and 3 mg/kg of the compound of Example 23 were administered iteratively for 15 weeks once a day. UTP, TG, and TC were measured according to a general method during the administration period at 4, 8, 12, and 15 weeks after the administration.

Figures 1, 4:
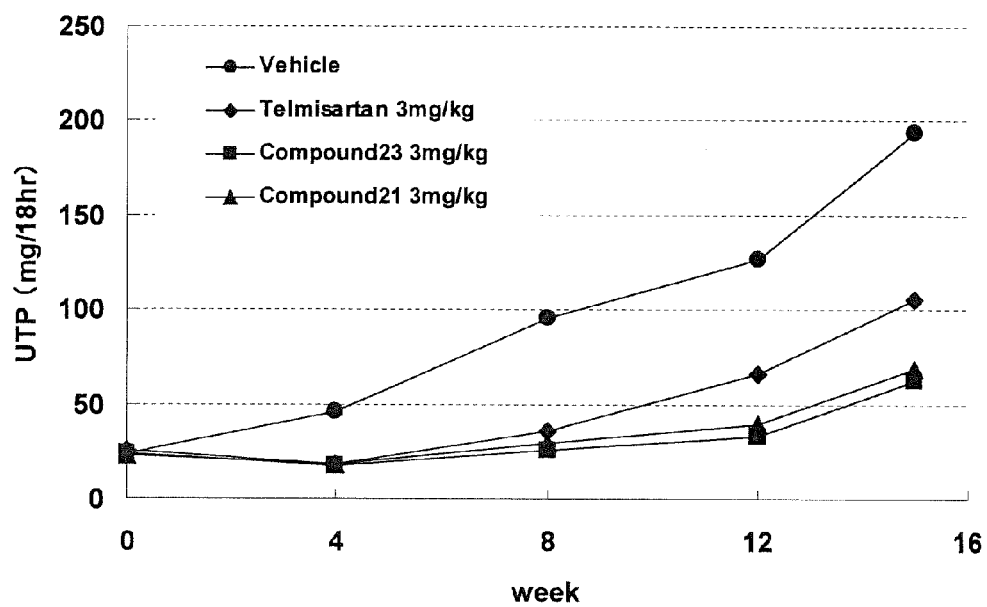
Figures 2, 4:
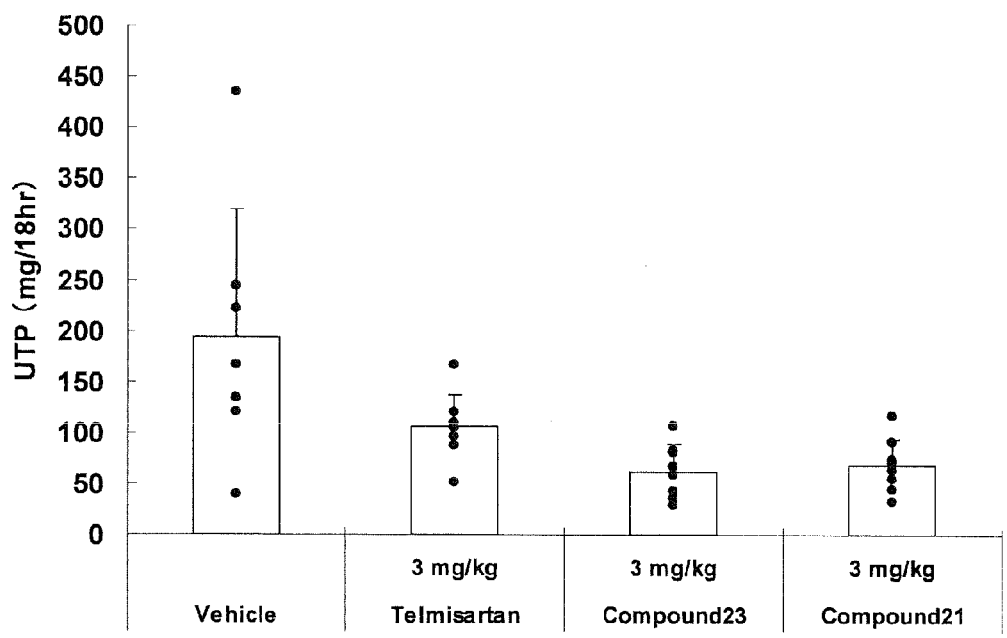
Figure 5:
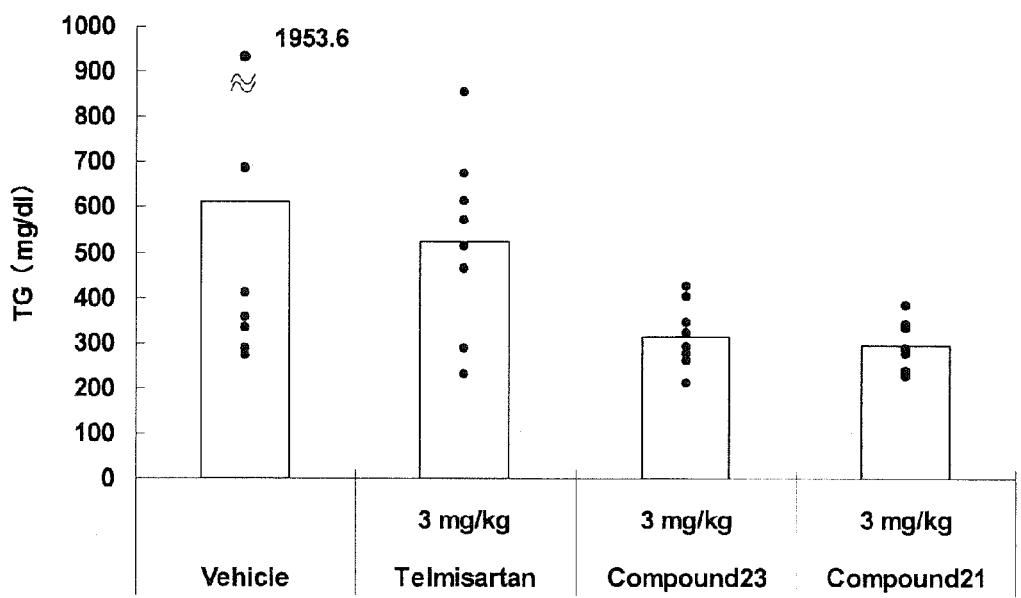
FIG. 5 illustrates results of investigations of activity for diabetic nephropathy. The vertical axis of FIG. 5 represents plasma triglyceride concentration, and Vehicle, Telmisartan, Compound 23, and Compound 21 of the horizontal axis represent solvent control, telmisartan, the compound of Example 23, and the compound of Example 21, respectively. The data in FIG. 5 represents individual values and average values of each individual.
Figure 6:
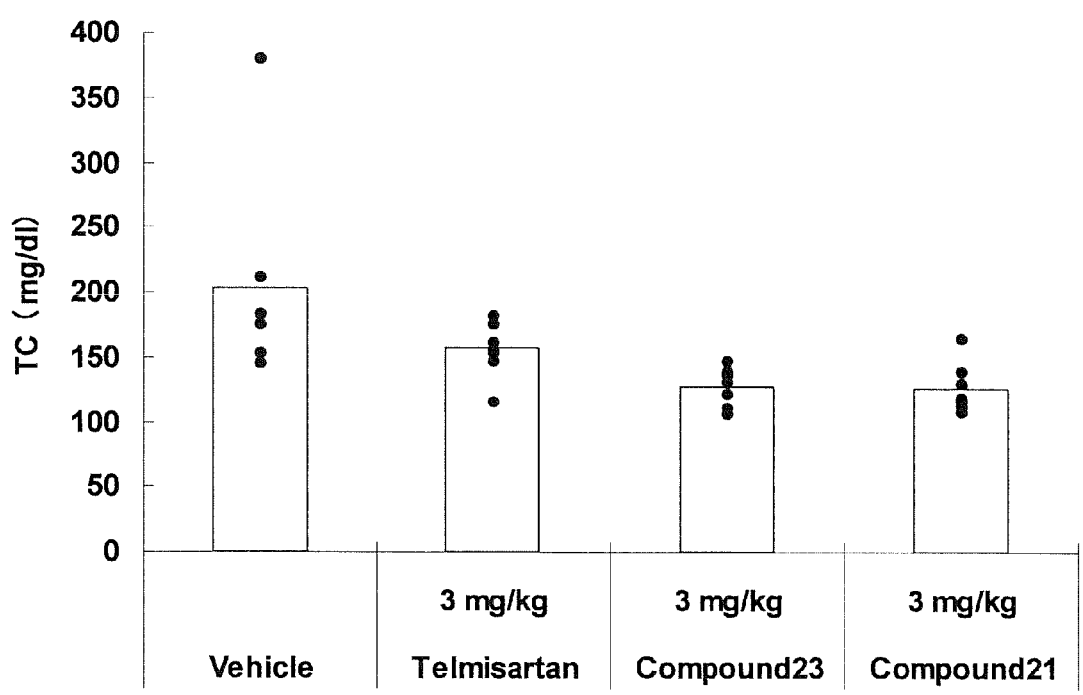
FIG. 6 illustrates results of investigations of activity for diabetic nephropathy. The vertical axis of FIG. 6 represents plasma total cholesterol concentration, and Vehicle, Telmisartan, Compound 23, and Compound 21 of the horizontal axis represent solvent control, telmisartan, the compound of Example 23, and the compound of Example 21, respectively. The data in FIG. 6 represents individual values and average values of each individual.

The results are shown in FIGS. 4, 5, and 6. Vehicle, Telmisartan, Compound 23, and Compound 21 in FIGS. 4, 5, and 6 represent solvent control, telmisartan, the compound of Example 23, and the compound of Example 21, respectively. The horizontal axis of FIG. 4-1 represents time (weeks after administration), and the vertical axis represents the elimination amount of urinary total protein per 18 hours. The data in FIG. 4-1 represents average values of each individual in each point, wherein -●- represents Vehicle (solvent control), -◆- represents Telmisartan, -■- represents Compound 23 (the compound of Example 23), and -▲- represents Compound 21 (the compound of Example 21). The vertical axis of FIG. 4-2 represents the elimination amount of urinary total protein per 18 hours. The data in FIG. 4-2 represents individual values and average values of each individual +standard deviation. As the results, the compound of Example 21 and the compound of Example 23 remarkably inhibited increase of the elimination amount of urinary total protein, and their activity was more potent than that of telmisartan.

The vertical axis of FIG. 5 represents the plasma triglyceride concentration. The data in FIG. 5 represents individual values and average values of each individual. As the results, the compound of Example 21 and the compound of Example 23 remarkably lowered the plasma triglyceride concentration, and such activity was not found in telmisartan.

The vertical axis of FIG. 6 represents the plasma total cholesterol concentration. The data in FIG. 6 represents individual values and average values of each individual. As the results, the compound of Example 21 and the compound of Example 23 remarkably lowered the plasma total cholesterol concentration, and such activity was more potent than that of telmisartan.

From these results, it was demonstrated that the compound of Example 21 and the compound of Example 23 have potent renal protecting activity, and inhibit occurrence or progress of diabetic nephropathy. Furthermore, it was believed that one reason for the potent activity may be related to improving activity of lipid metabolism, and it is believed that the potent activity is attributed to activities other than the angiotensin receptor antagonistic activity.

INDUSTRIAL APPLICABILITY

A phenylpyridine derivative represented by the formula (I) of the present invention or a salt thereof, or a solvate thereof is a novel compound that has both an angiotensin II receptor antagonistic activity and a PPARγ activation activity. The present invention provides the novel compound and a pharmaceutical composition containing the same. The compound of the present invention can be used as an effective component of a novel pharmaceutical product, i.e., a prophylactic and/or therapeutic agent for disorders involved with angiotensin II and PPARγ, for example, hypertension, heart diseases, angina pectoris, cerebrovascular disorders, cerebral circulatory disorders, ischemic peripheral circulatory disorders, renal diseases, arteriosclerosis, inflammatory diseases, type 2 diabetes, diabetic complications, insulin resistance syndrome, syndrome X, metabolic syndrome, and hyperinsulinemia, and therefore have an industrial applicability.

The invention claimed is:
1. A compound represented by the formula (I) below or a salt thereof, or a solvate thereof:

(I)

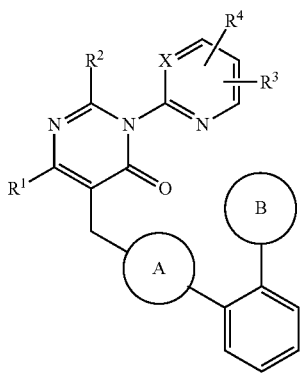

wherein, in the formula (I), ring A represents the following formula (II) or the following formula (III):

(II)

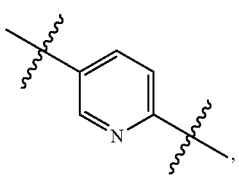

(III)

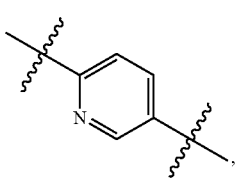

wherein, in the formula (I), Ring B represents the following formula (IV) or the following formula (V):

(IV)

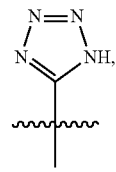

(V)

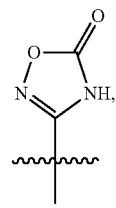

wherein X represents C—$R^5$ or a nitrogen atom,
wherein $R^1$ represents a $C_{1-6}$ alkyl group,
wherein $R^2$ represents a $C_{1-6}$ alkyl group or a $C_{3-8}$ cycloalkyl group, and
wherein $R^3$, $R^4$, and $R^5$ represent, independently from each other, a hydrogen atom, a halogen atom, a $C_{1-6}$ alkyl group, a halo $C_{1-6}$ alkyl group, or a $C_{1-6}$ alkoxy group which may have a substituent group, respectively.

2. The compound of claim 1 or salt thereof, or solvate thereof, wherein the compound represented by the formula (I) is a compound selected from a group consisting of:
5-{{6-[2-(1H-tetrazol-5-yl)phenyl]pyridin-3-yl}methyl}-6-butyl-3-(5-methoxypyrimidin-2-yl)-2-methylpyrimidin-4(3H)-one,
5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one,
5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one,
5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one,
5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one,
5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one,
5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one,
5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one,
5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one,
5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one,
5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one,
5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one, 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one, 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one, 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one, 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one, 5-{{5-[2-(1H-tetrazol-5-yl)phenyl]pyridin-2-yl}methyl}-6-butyl-2-methyl-3-(pyridin-2-yl)pyrimidin-4(3H)-one, 5-{{5-[2-(1H-tetrazol-5-yl)phenyl]pyridin-2-yl}methyl}-6-butyl-3-(5-methoxypyridin-2-yl)-2-methylpyrimidin-4(3H)-one, 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one, 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one, 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one, 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one, 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5(4H)-one, and 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one.

3. A pharmaceutical composition, comprising:
the compound of claim 1 or 2, or salt thereof, or solvate thereof, and
a pharmaceutically acceptable carrier.

* * * * *